(12) United States Patent
Boles et al.

(10) Patent No.: US 7,452,668 B2
(45) Date of Patent: Nov. 18, 2008

(54) ELECTROPHORETIC ANALYSIS OF MOLECULES USING IMMOBILIZED PROBES

(75) Inventors: Truett C. Boles, Waltham, MA (US); Andrew R. Muir, Cohasset, MA (US); Stephen J. Kron, Oak Park, IL (US); Ezra S. Abrams, W. Newton, MA (US)

(73) Assignee: Exact Sciences Corporation, Marlborough, MA (US)

( * ) Notice: Subject to any disclaimer, the term of this patent is extended or adjusted under 35 U.S.C. 154(b) by 228 days.

(21) Appl. No.: 10/888,767

(22) Filed: Jul. 9, 2004

(65) Prior Publication Data

US 2005/0079519 A1    Apr. 14, 2005

Related U.S. Application Data

(63) Continuation of application No. 08/971,845, filed on Aug. 8, 1997, now abandoned.

(60) Provisional application No. 60/046,708, filed on May 16, 1997.

(51) Int. Cl.
*C12Q 1/68* (2006.01)
*C12P 19/34* (2006.01)

(52) U.S. Cl. ......................................... 435/6; 435/91.1

(58) Field of Classification Search ........................ None
See application file for complete search history.

(56) References Cited

U.S. PATENT DOCUMENTS

| | | | |
|---|---|---|---|
| 4,034,428 A | 7/1977 | Jacuzzi | |
| 4,829,098 A | 5/1989 | Hoffman et al. | |
| 5,006,473 A | 4/1991 | Bouma et al. | |
| 5,176,966 A | 1/1993 | Epp et al. | |
| 5,215,882 A | 6/1993 | Bahl et al. | |
| 5,310,650 A | 5/1994 | McMahon et al. | |
| 5,478,893 A | 12/1995 | Ghosh et al. | |
| 5,482,836 A | 1/1996 | Cantor et al. | |
| 5,482,863 A | 1/1996 | Knobel et al. | |
| 5,518,900 A | 5/1996 | Nikiforov et al. | |
| 5,556,598 A | 9/1996 | Raybuck et al. | |
| 5,560,811 A | 10/1996 | Briggs et al. | |
| 5,610,287 A | 3/1997 | Nikiforov et al. | |
| 5,639,603 A | 6/1997 | Dower et al. | |
| 5,641,658 A | 6/1997 | Adams et al. | |
| 5,679,524 A | 10/1997 | Nikiforov et al. | |
| 5,679,773 A | 10/1997 | Holmes | |
| 5,723,344 A | 3/1998 | Mabilat et al. | |
| 5,741,639 A | 4/1998 | Ensing et al. | |
| 5,756,291 A * | 5/1998 | Griffin et al. .................... | 435/6 |
| 5,762,876 A | 6/1998 | Lincoln et al. | |
| 5,932,711 A | 8/1999 | Boles et al. | |
| 6,027,890 A | 2/2000 | Ness et al. | |
| 6,060,288 A | 5/2000 | Adams et al. | |
| 6,129,828 A | 10/2000 | Sheldon, III et al. | |
| 6,180,770 B1 | 1/2001 | Boles et al. | |
| 6,214,187 B1 | 4/2001 | Hammond et al. | |
| 6,238,927 B1 | 5/2001 | Abrams et al. | |
| 6,251,660 B1 | 6/2001 | Muir et al. | |
| 2002/0119480 A1 | 8/2002 | Weir et al. | |
| 2002/0123060 A1 | 9/2002 | Boles et al. | |
| 2002/0197614 A1 | 12/2002 | Weir et al. | |
| 2003/0138774 A1 | 7/2003 | Jones et al. | |
| 2003/0170635 A1 | 9/2003 | Hammond et al. | |

FOREIGN PATENT DOCUMENTS

| | | |
|---|---|---|
| EP | 0 703 296 A1 | 3/1996 |
| JP | 03-03-047097 * | 2/1991 |
| JP | HEI 06 (1994) 294796 | 10/1994 |
| WO | WO 90/07582 | 7/1990 |
| WO | WO-91/08307 | 6/1991 |
| WO | WO-91/13174 | 9/1991 |
| WO | WO-92/14843 | 9/1992 |
| WO | WO-92/15712 | 9/1992 |
| WO | WO-94/11530 | 5/1994 |
| WO | WO-94/16108 | 7/1994 |
| WO | WO-94/20831 | 9/1994 |
| WO | WO-97/27327 | 7/1997 |
| WO | WO-97/35033 | 9/1997 |
| WO | WO-97/41256 | 11/1997 |
| WO | WO-97/45554 | 12/1997 |
| WO | WO-97/45721 | 12/1997 |
| WO | WO-98/39351 | 9/1998 |
| WO | WO-98/51823 | 11/1998 |
| WO | WO-99/26724 | 6/1999 |
| WO | WO-99/30145 | 6/1999 |
| WO | WO-99/45374 | 9/1999 |
| WO | WO-99/66078 | 12/1999 |
| WO | WO-99/66079 | 12/1999 |
| WO | WO-00/20643 | 4/2000 |
| WO | WO-00/50644 | 8/2000 |

(Continued)

OTHER PUBLICATIONS

Baba, Molecular Biotechnology 6: 143 (1996).*

(Continued)

*Primary Examiner*—James Martinell
(74) *Attorney, Agent, or Firm*—Goodwin Procter LLP

(57) ABSTRACT

Methods of detecting target molecules using electrophoresis and media containing immobilized capture are described.

73 Claims, 4 Drawing Sheets

FOREIGN PATENT DOCUMENTS

| WO | WO-00/50870 | 8/2000 |
| --- | --- | --- |
| WO | WO-00/60118 | 10/2000 |
| WO | WO-00/60120 | 10/2000 |
| WO | WO-01/53817 | 7/2001 |

OTHER PUBLICATIONS

Baba et al. "Specific base recognition of oligodeoxynucleotides by capillary affinity gel electrophoresis using polyacrylamide-poly(9-vinyladenine) conjugated gel" Anal Chem. Sep. 1, 1992;64(17):1920-5.

Babe et al. "Base-specific separation of oligodeoxynucleotides by capillary affinity gel electrophoresis" Electrophoresis, 19:433-438 (1998).

Bartel et al. "HIV-1 Rev Regulation Involved Recognition of Non-Watson-Crick Base Pairs in Viral RNA" Cell, 67:529-539 (1991).

Biagioni et al., "A New Method for the Preparation of DNA-Cellulose" Analytical Biochemistry, 89:616-619 (Academic Press, Inc.) (1978).

Bock et al. "Selection of Single-Stranded DNA Molecules that Bind and Inhibit Human Thrombin" Nature, 355:564-566 (1992).

Botchkarev et al. "Neurotrophin-3 Involvement in the Regulation of Hair Follicle Morphogenesis" J. Inv. Dermatology, 111(3):279-285 (1998).

Ellington et al. "In Vitro Selection of RNA Molecules that Bind Specific Ligands" Nature, 346:818-822 (1990).

Famulok "Molecular Recognition of Amino Acids by RNA-Aptamers: An L-Citrulline Binding RNA Motif and its Evolution into an L-Arginine Binder" J. Am. Chem. Soc., 116:1698-1706 (1994).

Giver et al. "Selection and Design of High-Affinity RNA Ligands for HIV-1 Rev" Gene, 137:19-24 (1993).

Igloi "Variability in the stability of DNA-peptide nucleic acid (PNA) single-base mismatched duplexes: Real-time hybridization during affinity electrophoresis in PNA-containing gels" Proc. Natl. Acad. Sci. USA, 95:8562-8567 (Jul. 1998).

Iyer et al. "Accelerated Hybridization of Oglionucleotides to Duplex DNA" J. Biol. Chem., 270(24):14712-14717 (1995).

Jarrett "Affinity Chrolatography with Nucelic Acid Polymers" Chromatography, 618:315-339 (1993).

Jenison et al. "High-Resolution Molecular Discrimination by RNA" Science, 263:1425-1428 (1994).

Joyce "Amplification, Mutation and Selection of Catalytic RNA" Gene, 82:83-87 (1989).

Klug et al. "All you Wanted to Know about SELEC" Mol. Biol. Reports, 20:97-107 (1994).

Leclerc et al. "A Three-Dimensional Model of the Rev-Binding Element of HIV-1 Derived from Analyses of Aptamers" Structural Biology, 1(5):293-299 (1994).

Lorsch et al. "In Vitro Selection of RNA Aptamers Specific for Cyanocobalamin" Biochemistry, 33:973-982 (1994).

Moody et al. "Regiospecific Inhibition of DNA Duplication by Antisense Phosphate-Methylated Oligodexynucleotides" Nucleic Acids Res., 17 (12):4769-4782 (1989).

Muscate et al. "Capillary Affinity Gel Electrophoresis for Combined Size- and Sequence- Dependent Separation of Oglionucleotides" Anal. Chem., 70:1419-1424 (1998).

Nielsen et al. "Sequence-Selective Recognition of DNA by Strand Displacement with a Thymine-Substituted Polyamide" Science, 254:1497-1500 (1991).

Olejnik et al. "Photocleavable aminotag phosphoramidites for 5'-termini DNA/RNA labeling" Nucleic Acids Research, 26(15):3572-3576 (1998).

Ozaki et al. "Affinity Capillary Electrophoresis Using DNA Conjugates" Nucleic Acids Symposium Series, No. 37:235-236 (1997).

Paus et al. "Nerve Growth Factor Modulates Keratinocyte Proliferation in Murine Skin Organ Culture" British J. of Dermatology, 130:174-180 (1994).

Quesada "Replacement Polymers in DNA Sequencing by Capillary Electrophoresis" Analytical Biotechnology, 8:82-93 (1997).

Reinhartz et al. "A Novel Rapid Hybridization Technique: Paper Chromotography Hybridization Assay (PACHA)" Gene, 07525:221-226 (1993).

Sassanfar et al. "An RNA Motif that Binds ATP" Nature, 364:550-553 (1993).

Smith et al. "Covalent Binding of Proteins and Glucose-6-Phosphate Dehydrogenase to Cellulosic Carriers Activated with s-Triazine Tricholoride" Anal. Biochem., 61:392-41 (1974).

Smithies "An Improved Procedure for Starch-gels Electrophoresis: Further Variations in the Serum Proteins of Normal Individuals" Biochemical J., 71(3): 585-587 (1959).

Timofeev, et al. "Regioselective Imbolization of Short Oligonucleotides to Acrylic Copolymer Gels" Nucleic Acids Res., 24(16):3142-3148 (1996).

Tsurui et al. "A Rapid and Efficient Cloning Method with a Solid-Phase DNA Probe: Application for Cloning the 5'—Flanking Region of the Gene Encoding Human Fibronectin" Gene, 88:233-239 (1990).

Tuerk et al. "Systematic Evolution of Ligands by Exponential Enrichment: RNA Ligands to Bacteriophage T4 DNA Polymerase" Science, 249:505-511 (1990).

Van Ness et al. "A Versatile Solid Support System for Oligodeoxynucleotide Probe-Based Hybridization Assays" Nuc. Acids Res. 19(12):3345-3350 (1991).

Wagner "Gene Inhibition Using Antisense Oligodexynucleotides," Nature, 372:333-335 (1994).

Weider et al. "One Hundred-Fold Acceleration of DNA Renaturation Rates in Solution" Biopolymers, 20:1537-1547 (1981).

Wetmur "Acceleration of DNA Renaturation Rates" Biopolymers, 14:2517-2524 (1974).

Wetmur, "DNA Probes: Applications of the Principles of Nucleic Acid Hybridization" Critical Rev. in Biochem. and Mol. Biol., 26(3/4):227-259 (1991).

Yokota et al. "Differential Cloning of Genomic DNA: Cloning of DNA with an Altered Primary Structure by in-gel Competitive Reassociation" Proc. Natl. Acad. Sci. USA, 87:6398-6402 (1990).

International Search Report for PCT/US98/09952, dated Mar. 9, 1998.

Office Action dated Oct. 23, 2007 cited in corresponding Japanese Patent Application No. 10-549576.

Office Action dated Jun. 17, 2008 cited in corresponding Japanese Patent Application No. 10-549576.

\* cited by examiner

ELECTROPHORETIC ANALYSIS OF MOLECULES USING IMMOBILIZED PROBES

RELATED APPLICATIONS

This application is a Continuation of U.S. Ser. No. 08/971,845, filed Aug. 8, 1997, now abandoned which claims priority to Provisional Application No. 60/046,708, filed May 16, 1997, the teachings of which are herein incorporated, in their entirety, by reference.

BACKGROUND OF THE INVENTION

Nucleic acid base pairing is an extremely high affinity and specific interaction. For this reason, nucleic acid hybridization assays have been devised for a variety of diagnostic purposes.

Under laboratory conditions, hybridization assays can be extraordinarily sensitive, detecting femtogram amounts of a specific molecule. However, several technical limitations have prevented widespread use of hybridization analysis in commercial diagnostic techniques.

First, use of high activity hybridization probes requires stringent procedures for separating unhybridized (or improperly hybridized) and hybridized probe. This separation can be facilitated by the use of solid phase hybridization formats, in which either the sample nucleic acid or the probe that is complementary to the desired target is immobilized on a solid support. In the latter strategy, the immobilized probe, hereafter referred to as the "capture" probe, is usually unlabeled, and the hybridization is detected by a second hybridization probe that binds the sample at a position separate from that recognized by the capture probe. Hybridized and unhybridized species can be separated by washing the support.

A second limitation of hybridization assays is that efficient hybridization of samples containing low concentrations of target nucleic acids frequently requires lengthy incubations (up to several hours) under carefully controlled conditions. Unfortunately, use of solid phase assays exacerbates this problem, since immobilized nucleic acids virtually always hybridize with slower kinetics than nonimmobilized ones.

For these reasons, a number of workers have sought methods to perform solid phase hybridizations with better kinetics and efficiency. Several groups have found that inclusion of high molecular weight polymers such as dextran sulfate or polyethylene glycol improves solid phase assay performance, albeit modestly. (Wieder and Wetmur, *Biopolymers,* 20:1537 (1981); Wetmur, *Biopolymers,* 14:2517 (1975); Yokota and Oishi, *Proc. Natl. Acad. Sci. USA,* 87:6398 (1990)). Several groups have developed chromatographic solid phase hybridization methods that show improvements. In general, it has been found that flowing the solution phase nucleic acid strand over (or through) the solid support bearing the immobilized strand improves both kinetics and efficiency of hybridization. MacMahon and Gordon, U.S. Pat. No. 5,310,650, describes immobilized target molecules on nitrocellulose filters, with labeled probe flowing through the immobilized target regions by capillary action. In a similar experiment, Reinhartz et al., *Gene,* 136:221-226 (1993)) immobilized capture probes on paper filters and flowed labeled single-stranded PCR products through the capture probe region, again using capillary action. Others have demonstrated improved hybridization assays by passing samples through an HPLC column containing silica particles covalently modified with capture probes. (Tsurui et al., *Gene,* 88:233-239 (1990)).

However, despite these advances, there remains a need for a hybridization analysis method that is not only accurate, but fast, efficient and simple to use.

SUMMARY OF THE INVENTION

The present invention relates to the discovery that nucleic acids and nucleic acid analogs can be covalently attached (immobilized) to an electrophoretic medium and that electrophoresis can be used to separate, purify or analyze target molecules that specifically bind to (e.g., associate with), or are specifically bound by, the immobilized nucleic acids, or nucleic acid analogs. The immobilized nucleic acids, or nucleic acid analogs, are referred to herein as capture probes. These immobilized capture probes can be used to analyze a variety of molecules. One specific binding reaction encompassed by the present invention is hybridization. With hybridization, capture probes are typically nucleic acids comprising nucleotide sequences that are substantially complementary to the nucleotide sequences of the target nucleic acid so that specific hybridization results. Additionally, nucleic acid analogs such as peptide nucleic acids (PNA) can be covalently attached to the electrophoretic medium for use as capture probes. The capture probes, being immobilized within the medium used for electrophoretic separation, results in the target nucleic acid that specifically hybridizes with the capture probe also becoming immobilized in the matrix. As used herein, the term "matrix" refers to the immobilized polymeric components of the electrophoretic medium which provide the molecular sieving properties of the medium, and also provide the means for immobilization of the capture probes. Examples of suitable matrix materials include gel-forming polymers such as cross-linked polyacrylamide, agarose, and starch. Non-gel-forming polymers such as linear polyacrylamide, poly(N,N-dimethylacrylamide), poly(hydroxyethylcellulose), poly(ethyleneoxide) and poly(vinlyalcohol), as commonly used in capillary electrophoresis applications, can also serve as suitable matrices.

The present invention specifically relates to methods, and apparatus to carry out the methods of analysis described herein, in which electrophoresis is used to move solution phase target molecules into contact with a capture probe that is immobilized on a suitable electrophoresis matrix.

The methods of the present invention are applicable to analysis of any chemical entity that can be electrophoresed (e.g., a charged molecule that has detectable mobility when placed in an electrophoretic field) and that binds to, or is bound by, nucleic acids. Such entities include, for example, DNA or RNA samples, nucleic acid binding proteins, and aptamer binding partners (aptamers are nucleic acids that are selected to bind to specific binding partners such as peptides, proteins, drugs, polysaccharides and small organic molecules, e.g., theophylline and caffeine; Jenison, et al., *Science,* 263:1425-1429 (1994)). For example, methods described herein can be used for analysis and purification of target nucleic acids using immobilized capture probes, where specific binding involves base pairing interactions between sample nucleic acids and the capture probe, as in nucleic acid hybridization. The methods described herein are also useful for purification of sequence-specific nucleic acid binding proteins, since synthetic nucleic acids of defined sequence can be immobilized in matrices commonly used for protein electrophoresis.

The test sample can be from any source and can contain any molecule that can form a binding complex with a capture probe. Specifically encompassed by the present invention are samples from biological sources containing cells, obtained using known techniques, from body tissue (e.g., skin, hair, internal organs), or body fluids (e.g., blood, plasma, urine, semen, sweat). Other sources of samples suitable for analysis by the methods of the present invention are microbiological samples, such as viruses, yeasts and bacteria; plasmids, isolated nucleic acids and agricultural sources, such as recombinant plants.

The test sample is treated in such a manner, known to those of skill in the art, so as to render the target molecules contained in the test sample available for binding. For example, if the target molecule is a nucleic acid present in a cell, a cell lysate is prepared, and a crude cell lysate (e.g., containing the target nucleic acid as well as other cellular components such as proteins and lipids) can be analyzed. Alternatively, the target nucleic acids can be isolated (rendering the target nucleic acids substantially free from other cellular components) prior to analysis. Isolation can be accomplished using known laboratory techniques. The target nucleic acid can also be amplified (e.g., by polymerase chain reaction or ligase chain reaction techniques) prior to analysis.

The test sample is then introduced into a suitable electrophoretic medium. The capture probes are immobilized within the electrophoresis matrix by direct attachment to the medium, or by attachment to particles that are suspended and trapped within the matrix. In either case, the capture probes are immobilized, that is, they do not migrate under the influence of the applied electric field.

The test sample containing the target molecule can be detectably labeled before, during, or after the electrophoresis step. Detecting the presence of target molecule/capture probe complexes immobilized in the matrix is indicative of the presence of the target molecule that specifically binds to, or is bound by, the capture probe. Once the test sample is introduced into the electrophoretic medium it is subjected to an electrical field resulting in the electrophoretic migration of the test sample through the matrix, under conditions and time sufficient for the target molecule, of the test sample, if present, to bind to one, or more, capture probes, resulting in target molecule/capture probe complexes immobilized in the matrix. Typical voltage gradients used in nucleic acid electrophoresis procedures range from approximately 1 V/cm to 100 V/cm. Other field strengths may be useful for certain highly specialized applications.

The target immobilization may be transient or stable for a substantial time period, depending on the strength and lifetime of the target/capture probe binding complex. In one embodiment of the present invention, the target molecule transiently binds to, or associates with, one or more capture probes immobilized in the matrix. In this embodiment the target molecule may bind and be released multiple times during migration through one more regions of the electrophoretic matrix containing immobilized capture probes. The electrophoretically induced migration is thereby hindered and delayed, such that the migration rate is slower than if no such binding occurred, and the time to migrate through the subject region and the matrix is increased. The rate of migration of the target molecule within the electrophoretic matrix is measured, and can be compared with migration rate of the target molecule in a reference (e.g. control) experiment. As used herein, the control experiment is an equivalent experiment with substantially similar, or equivalent, materials and conditions, except that no capture probes are immobilized in the matrix. Alternatively a control experiment can be a similar experiment corrected for differences from exact equivalence of the test experiment, or can be a sufficiently similar experiment that no such corrections are necessary to obtain analytical results.

If, in a particular experiment, the migration rate of a molecule is found to be slower than the migration rate of the molecule in a reference experiment, this delayed migration indicates that the molecule is the target molecule that associates with one or more capture probes contained in the matrix. Furthermore, the degree of reduction, or decrease, in the target molecule migration rate is indicative of the following: the affinity of binding of the target molecule with the one or more capture probes; the concentration of capture probes immobilized within the matrix; and the extent of the capture probe region or regions traversed in migration through the matrix.

Alternatively, the migration rate of the target molecule may be compared with the migration rate of a control molecule with known migration rate under the experimental conditions. The relative migration times of the target molecule migrating through a matrix with one or more immobilized capture probes associating with the target molecule, and the migration rate of the control molecule under substantially similar, or equivalent, conditions but with no such association, are empirically determined or calculated from their molecular properties.

If, under experimental conditions the similar, or relative migration rates of a putative target (e.g., test) molecule and the control molecule are substantially equivalent (e.g., in the correct or expected relationship) this indicates that the test molecule is actually the target molecule of interest and that the matrix contains one or more immobilized capture probes that associate with the target molecule. Alternatively, the same indication can be obtained from the relative migration distances achieved in the matrix containing the subject capture probes, for the target molecule and the test molecule, after similar migration times under substantially similar, or experimental conditions.

A typical analytical situation is where the migration rate of the control molecule is substantially similar to, or equivalent to, that of the target molecule in a matrix that does not contain the immobilized capture probes but is otherwise similar. The control molecule and test molecule will achieve similar migration rates and times if the test molecule is not the expected target molecule, which would associate with one or more capture probes. However, the control molecule will achieve a faster migration rate and a shorter migration time than a test molecule migrating through a region of matrix containing immobilized capture probes if the test molecule is the target molecule. Most typically, such analysis can be achieved in parallel, with both the control molecule and the test molecule being substantially simultaneously electrophoresed through one or more regions of the same matrix, and their relative migration rates, or migrations times, being monitored or measured continuously, or measured after one or more fixed migration or time periods.

Electrophoretic matrices useful for the methods described herein can be provided in a number of different formats. For example, the matrix can be provided in a format where its physical length significantly exceeds its breadth or depth, e.g. contained within a tube or formatted as a narrow strip. Alternatively, the matrix can be provided in a format where its length and breadth significantly exceed its depth, e.g. as a relatively thin layer on a surface or formatted as a slab. Alternatively, the matrix can be provided essentially as a solid body, where its length, breadth and depth are of the same order, e.g. as an actual or approximately rectilinear, polygonal, spherical, ellipsoid solid or similar physical form.

Positional arrangements of immobilized capture probes useful for the methods described herein can also be provided in a number of different formats. For example, the matrix can contain one or more capture probes, homogeneously distributed throughout the entire matrix or in one or more regions of the matrix. Also, two or more regions of similar or different immobilized capture probes, or combinations of probes, can be positioned such that a sample migrates through the sequence of capture probe regions when migrating through the matrix. Alternatively, multiple regions of immobilized capture probes can be positioned such as to form two or more migration paths, each of which passes through one or a sequence of immobilized capture probe regions.

Thus, as a result of the work described herein, methods and apparatus are now available for fast, efficient and accurate electrophoretic analysis of target molecules using immobilized capture probes that specifically bind to the target molecule.

BRIEF DESCRIPTION OF THE FIGURES

FIG. 3A depicts a gel containing immobilized probes that are complementary to normal sequences.

DETAILED DESCRIPTION OF THE INVENTION

Figure 1:
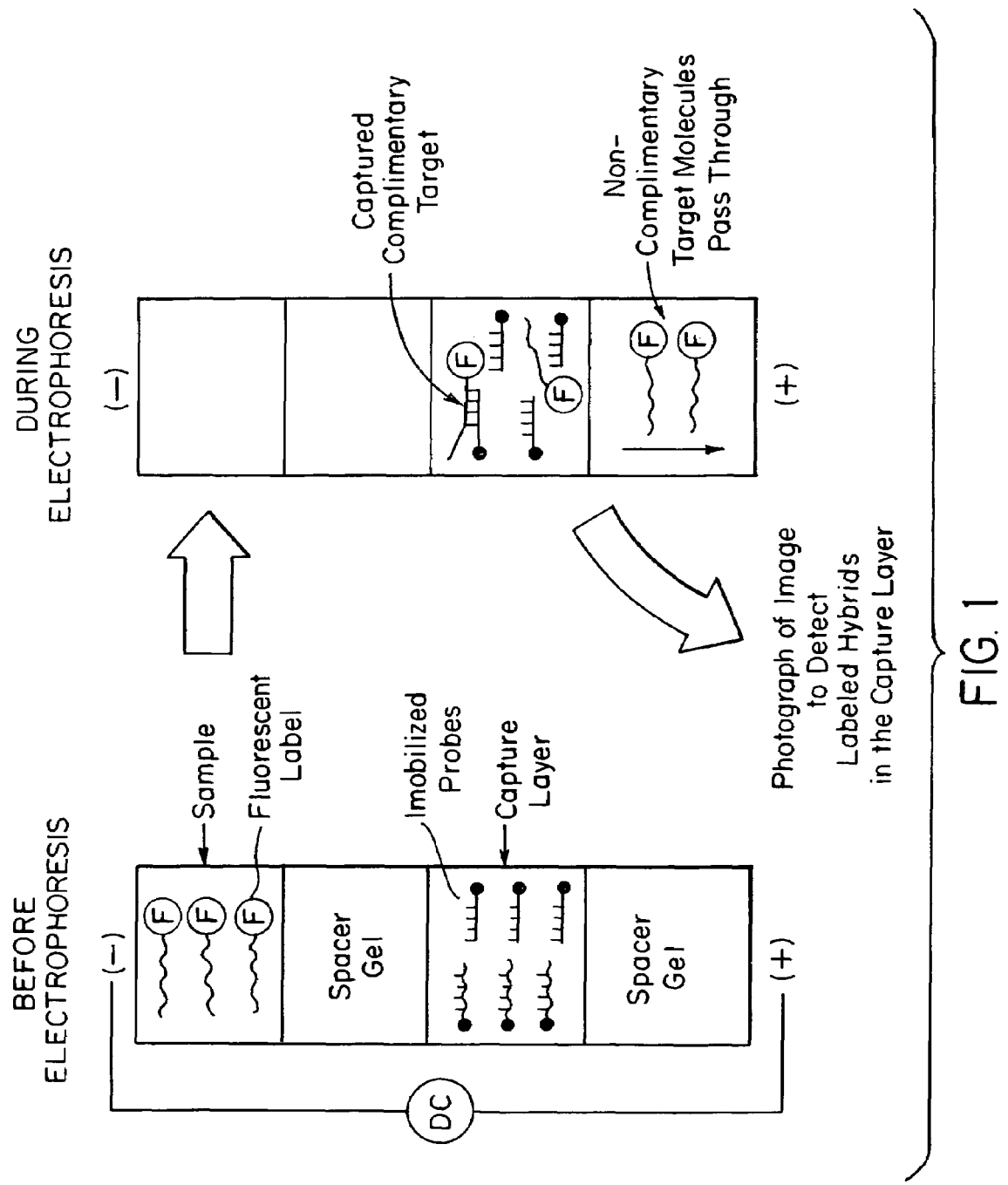
FIG. 1 is a graphic depiction of the principle of the electrophoretic analysis using immobilized capture probes.

The present invention relates to electrophoretic methods to analyze specific binding reactions in which capture probes are covalently attached to (e.g., immobilized in) the electrophoretic matrix. The capture probes are nucleic acids or nucleic acid analogs that specifically bind to, or hybridize with target molecules present in a test sample. The test sample is introduced into the electrophoretic matrix and subjected to an electrical field, under conditions suitable for the specific binding of the target molecule to the capture probe. The immobilized probes are attached internally throughout the electrophoretic matrix, and binding takes place within the matrix. FIG. 1 is a schematic representation which illustrates the principle of electrophoretic capture analysis.

Electrophoretic Matrices

Any matrix suitable for electrophoresis can be used for the methods of the present invention. Suitable matrices include acrylamide and agarose, both commonly used for nucleic acid electrophoresis. However, other materials may be used. Examples include chemically modified acrylamides, starch, dextrans, cellulose-based polymers. Examples include modified acrylamides and acrylate esters (for examples see Polysciences, Inc., Polymer & Monomer catalog, 1996-1997, Warrington, Pa.), starch (Smithies, Biochem. J., 71:585 (1959); product number S5651, Sigma Chemical Co., St. Louis, Mo.), dextrans (for examples see Polysciences, Inc., Polymer & Monomer Catalog, 1996-1997, Warrington, Pa.), and cellulose-based polymers (for examples see Quesada, Current Opin. in Biotechnology, 8:82-93 (1997)). Any of these polymers listed above can be chemically modified to allow specific attachment of capture probes for use in the present invention.

Specifically encompassed by the present invention are the use of nucleic acids of nucleic acid analogs as capture probes. Methods of coupling nucleic acids to create nucleic acid-containing gels are known to those of skill in the art. Nucleic acids and nucleic acid analogs can be coupled to agarose, dextrans, cellulose, and starch polymers using cyanogen bromide or cyanuric chloride activation. Polymers containing carboxyl groups can be coupled to synthetic capture probes having primary amine groups using carbodiimide coupling. Polymers carrying primary amines can be coupled to amine-containing probes with glutaraldehyde or cyanuric chloride. Many polymers can be modified with thiol-reactive groups which can be coupled to thiol-containing synthetic probes. Many other suitable methods are known in the literature. (For review see Wong, "Chemistry of Protein Conjugation and Cross-linking", CRC Press, Boca Raton, Fla., 1993).

Methods for covalently attaching the capture probes described herein to polymerizable chemical groups have also been developed. When copolymerized with suitable mixtures of polymerizable monomer compounds, matrices containing high concentrations of immobilized nucleic acids can be produced. Examples of methods for covalently attaching nucleic acids to polymerizable chemical groups are found in U.S. Ser. No. 08/812,105, entitled "Nucleic Acid-Containing Polymerizable Complex," the teachings of which are herein incorporated by reference, in their entirety.

For some methods, it may be useful to use composite matrices, containing a mixture of two or more matrix forming materials. An example is the composite acrylamide-agarose gel. These gels typically contain from 2-5% acrylamide and 0.5%-1% agarose. In these gels the acrylamide provides the chief sieving function, but without the agarose, such low concentration acrylamide gels lack mechanical strength for convenient handling. The agarose provides mechanical support without significantly altering the sieving properties of the acrylamide. In such cases, the nucleic acid can be attached to the component that confers the sieving function of the gel, since that component makes most intimate contacts with the solution phase nucleic acid target.

For many applications gel-forming matrices such as agarose and cross-linked polyacrylamide will be preferred. However, for capillary electrophoresis (CE) applications it is convenient and reproducible to use soluble polymers as electrophoretic matrices. Examples of soluble polymers that have proven to be useful for CE analyses are linear polymers of polyacrylamide, poly(N,N-dimethylacrylamide), poly(hydroxyethylcellulose), poly(ethyleneoxide) and poly(vinylalcohol) as described in Quesada (*Current Opinion in Biotechnology*, vol. 8, pp. 82-93, 1997). These soluble matrices can also be used to practice the methods of the present invention. It is particularly convenient to use the methods found in the application U.S. Ser. No. 08/812,105, entitled "Nucleic Acid-Containing Polymerizable Complex" for preparation of soluble polymer matrices containing immobilized capture probes. A detailed example of this strategy, which involves copolymerization of ethylene-containing capture probes during polymer formation, is given in Example 5 below. Another approach for attaching oligonucleotide probes to preformed polyacrylamide gels (Timofeev, et al., Nucleic Acids Res. 24, 3142-3148, 1996), can also be used to attach capture probes to prepolymerized soluble linear polyacrylamide.

Nucleic acids may be attached to particles which can be incorporated into electrophoretic matrices. The particles may be macroscopic, microscopic, or colloidal in nature. (see Polyciences, Inc., 1995-1996 particle Catalog, Warrington, Pa.). Cantor, et al., U.S. Pat. No. 5,482,863 describes methods for casting electrophoresis gels containing suspensions or particles. The particles are linked to nucleic acids using methods similar to those described above, mixed with gel forming compounds, and cast as a suspension into the desired matrix form.

Immobilized Probes for Analysis of Hybridization Binding Reactions

A variety of capture probes can be used in the methods of the present invention. Typically, the capture probes of the present invention comprise a nucleic acid with a nucleotide sequence substantially complementary to the target molecule wherein the target molecule hybridizes to the capture probe. The complementarity of nucleic acid capture probes need only be sufficient enough to specifically bind the target molecule and demonstrate the presence or absence of the target molecule. Probes suitable for use in the present invention comprise RNA, DNA, nucleic acid analogues, and chimeric probes of mixed class comprising a nucleic acid with another organic component, e.g., peptide nucleic acids. Capture probes can be single-stranded or double-stranded nucleic acids.

As defined herein, the term "nucleic acid" includes DNA or RNA. Nucleic acids referred to herein as "isolated" are nucleic acids separated away from the components of their source of origin (e.g., as it exists in cells, or a mixture of nucleic acids such as a library) and may have undergone further processing. Isolated nucleic acids include nucleic acids obtained by methods known to those of those of skill in the art. These isolated nucleic acids include substantially pure nucleic acids, nucleic acids produced by chemical synthesis, by combinations of biological and chemical methods and recombinant nucleic acids which are isolated.

"Nucleic acid analogs", as used herein, include nucleic acids containing modified sugar groups, phosphate groups or modified bases. Examples of nucleic acids having modified bases, include, for example, acetylated, carboxylated or methylated bases (e.g., 4-acetylcytidine, 5-carboxymethylaminomethyluridine, 1-methylinosine, norvaline or allo-isoleucine). Such nucleic acid analogs are known to those of skill in the art.

As defined herein, "substantially complementary" means that the nucleotide sequence of the capture probe need not reflect the exact nucleotide sequence of the target molecule, but must be sufficiently similar in identity of sequence to hybridize with the target molecule under specified conditions. For example, non-complementary bases, or additional nucleotides can be interspersed in sequences provided that the sequences have sufficient complementary bases to hybridize therewith.

Specified conditions of hybridization can be determined empirically by those of skill in the art. For example, conditions of stringency should be chosen that significantly decrease non-specific hybridization reactions. Stringency conditions for nucleic acid hybridizations are explained in e.g., *Current Protocols in Molecular Biology*, Ausubel, F. M., et al., eds., Vol. 1, Suppl, 26, 1991, the teachings of which are herein incorporated by reference, in their entirety. Factors such as probe length, base composition, percent mismatch between the hybridizing sequences, temperature and ionic strength influence the stability of nucleic acid hybrids. Stringent conditions, e.g., moderate, or high stringency, can be determined empirically, depending on part on the characteristics of the probe and target molecule.

Typically, the length of a capture probe will be at least 5 nucleotides in length, more typically between 5 and 50 nucleotides, and can be as long as several thousand bases in length.

Probes containing modified nucleotides may also be useful. For instance, nucleotides containing deazaguanine and uracil bases may be used in place of guanine and thymine-containing nucleotides to decrease the thermal stability of hybridized probes (Wetmur, *Critical reviews in Biochemistry and Molecular Biology*, vol. 26, pp. 227-259, 1991). Similarly, 5-methylcytosine can be substituted for cytosine if hybrids of increased thermal stability are desired (Wetmur, *Critical reviews in Biochemistry and Molecular Biology*, vol. 26, pp. 227-259, 1991). Modifications to the ribose sugar group, such as the addition of 2'-O-methyl groups can reduce the nuclease susceptibility of immobilized RNA probes (Wagner, *Nature*, vol. 372, pp. 333-335, 1994). Modifications that remove negative charge from the phosphodiester backbone can increase the thermal stability of hybrids (Moody et al. *Nucleic Acids Res.*, vol. 17, pp. 4769-4782, 1989; Iyer et al. *J. Biol. Chem.*, vol. 270, pp. 14712-14717, 1995).

Nucleic acid analogues can also be useful as immobilized probes. One example of a useful nucleic acid analogues is peptide nucleic acid (PNA), in which standard DNA bases are attached to a modified peptide backbone comprised of repeating N-(2-aminoethyl)glycine units (Nielsen et al., Science vol. 254, pp. 1497-1500, 1991). The peptide backbone is capable of holding the bases at the proper distance to base pair with standard DNA and RNA single strands. PNA-DNA hybrid duplexes are much stronger than equivalent DNA-DNA duplexes, probably due to the fact that there are no negatively charged phosphodiester linkages in the PNA strand. In addition, because of their unusual structure PNAs are very resistant to nuclease degraded. For these reasons, PNA nucleic acid analogues are useful for immobilized probe assays. It will be apparent to those skilled in the art that similar design strategies can be used to construct other nucleic acid analogues that will have useful properties for immobilized probe assays.

Single and Double Stranded Target Molecules

In one embodiment of the present invention, a single-stranded target molecule and a single-stranded immobilized probe is used. This embodiment is especially useful for analysis of RNA targets. It is also useful for capture of specific targets from complex samples where renaturation of target is not rapid. Highly concentrated targets, such as PCR products, may require denaturation immediately prior to electrophoresis because of rapid renaturation. For example, for analysis of PCR products 100-250 base pairs in length, it is convenient to bring the sample to 75% formamide (volume/volume) and heat at 60° for 5 minutes immediately prior to electrophoresis.

In another embodiment of the present invention, a double-stranded target is captured by a single-stranded immobilized probe. For example, probes can be designed that will associate with double-stranded nucleic acids to form a triple-stranded structure. The third strand locates in the major groove of the duplex and forms Hoogsteen base pairing interactions with the bases of the duplex (Hogan and Kessler, U.S. Pat. No. 5,176,966 and Cantor, et al., U.S. Pat. No. 5,482,836). The design of the probe is therefore subject to the constraints governing those chemical interactions. However, the frequency of sequences capable of forming triplex structures in naturally occurring nucleic acids is high enough that many target nucleic acids can be specifically captured using this probe design strategy.

Alternatively, capture probes can be designed that will associate with double-stranded nucleic acids by formation of displacement loop formation. Such probes bind to only one strand of the duplex nucleic acid and displace the probe-homologous duplex strand of the duplex locally. This displacement can only be achieved if the probe-target strand interaction is much more favorable than the interaction between the target strands. Such probes can be made using modified bases and techniques described in Wetmur, *Critical Reviews in Biochemistry and Molecular Biology*, Vol 26, pp 227-259 (1991), backbone modifications (Moody, et al., *Nucleic Acids Res.*, vol. 17, pp. 4769-4782 (1989)) and nucleic acid analogues (Nielson, et al., *Science*, 254:1497-1500 (1991). The use of peptide nucleic acid (PNA) probes, which base pair exceptionally tightly and specifically with naturally occurring nucleic acids would be especially useful in this embodiment.

Immobilized Capture Probes and Targets for Analysis of Nucleic Acid Binding Proteins The methods of the present invention are also useful for analysis of nucleic acid binding proteins. In these cases, the nucleic acids that are selected mimic, in some way, the protein's natural binding substate.

Both sequence-specific and non-sequence-specific nucleic acid binding proteins can be analyzed. For analysis of sequence-specific binding proteins, the capture probe is designed to contain the sequence which is recognized by the target binding protein. For analysis of non-specific interactions, mixtures of capture probes can be used, to ensure that any observed binding is not dependent on any particular nucleic acid sequence.

Electrophoretic analysis is performed under conditions which allow the protein to retain its native structure, thereby permitting the protein to bind to the capture probe during electrophoresis. Following electrophoresis, the presence of the protein within the gel region containing the immobilized capture probe can be detected by staining with colored or fluorescent dyes, autoradiography (if the sample has been radioactively labeled), silver staining, and various other standard methods well known to those of skill in the art of protein electrophoresis.

For detection and analysis of sequence-specific DNA binding proteins that are important in transcriptional regulation, it is particularly useful to utilize double-stranded capture probes. In this implementation, a double-stranded capture probe containing a sequence known (or suspected) to be recognized by the protein target is used. The test sample is electrophoresed through the region containing the capture probe. Following electrophoresis, the position of the protein within the gel is determined. The presence of protein in the gel region containing the capture probe indicates the presence of a DNA binding-protein in the sample. Control experiments demonstrating that binding does not occur with a DNA capture probe that does not carry the specific sequence of interest can be used to demonstrate the sequence specificity of the binding.

Single stranded capture probes may also be useful. For instance, single-stranded RNA capture probes can be used for detection and purification of proteins that bind to specific RNA sequences. Single-stranded DNA probes may be useful for detecting regulatory proteins of viruses that contain single-stranded DNA genomes, or proteins that bind specifically to single-stranded DNA segments within replication origins.

Aptamer Capture Probes

Several groups have developed methods for screening random libraries of nucleic acids for molecules that exhibit selected desirable binding properties or catalytic capabilities (Ellington and Szostak, *Nature*, 346:818-822 (1990); Joyce, *Gene*, 82:83-87 (1989) Tuerk and Gold, *Science*, 249:505-501 (1990)). For many applications, these libraries consist of random pools of oligonucleotides (RNA or DNA) generated on standard, commercially available nucleic acid synthesizers. Libraries of up to $10^{15}$ individual sequences 25 bases in length can be constructed routinely (Klug and Famulok, *Molec. Biol. Reports*, 20:97-107, (1994)). This pool is then screened for functional binding to the desired target. Oligonucleotides capable of binding the target are separated by column chromatography, filter binding, or other appropriate methods for purifying probe/target binding complexes. The bound oligonucleotides are purified, and usually the bound pool is amplified by the polymerase chain reaction, using primers that recognize defined sequences that flank the region of randomized sequence. Additional cycles of target binding and re-amplification can be performed as needed to enrich for oligonucleotide probes that bind with high affinity. Members of the final pool are cloned using recombinant DNA techniques, sequenced, and analyzed to identify sequence elements responsible for target binding.

Nucleic acid binding probes of this type, termed aptamers, can be selected against virtually any target molecule. To date, aptamers have been selected that are capable of forming specific tight binding complexes with specific proteins (Bartel, et al., *Cell*, 67:529-536 (1991); Giver, et al., *Gene*, 137:19-24 (1993); Leclerc, et al, *Nature Struct. Biol.*, 1:293-299; Bock, et al., *Nature*, 355:564-566 (1992)), amino acids (Famulok, *J. Am. Chem. Soc.*, 116:1698-1706 (1994)), small molecule drugs (Jenison, et al., *Science*, 263:1425-1429, 1994)), vitamins (Lorsch and Szostak, *Biochemistry*, 33:973-982 (1994)), and nucleotide cofactors (Sassanfar and Szostak, *Nature*, 364:550-553 (1993)).

The present invention provides a convenient platform technology for using aptamers in preparative and analytical applications. Once an appropriate aptamer has been selected, it can be attached to an appropriate electrophoretic medium for use as a capture probe. The test sample is electrophoresed through the capture zone, and subsequently the capture zone is analyzed for the presence of target. For preparative applications, target molecules can be eluted from the capture zone after allowing non-target sample components to migrate out of the medium. Since aptamers can be selected against virtually any target, the use of aptamer capture probes allows the methods of the present invention to be used for the electrophoretic analysis and purification of a wide variety of target molecules. It is important to note that any molecule is suitable for analysis in the methods of the present invention as long as the molecule is charged under the conditions used for electrophoresis, (e.g., the target molecule has a detectable mobility when placed in an appropriate electrophoretic medium) so that it will migrate under the influence of the applied electric field.

Uniformly Modified Electrophoretic Media for Analysis of Target Molecules

Figure 2B:
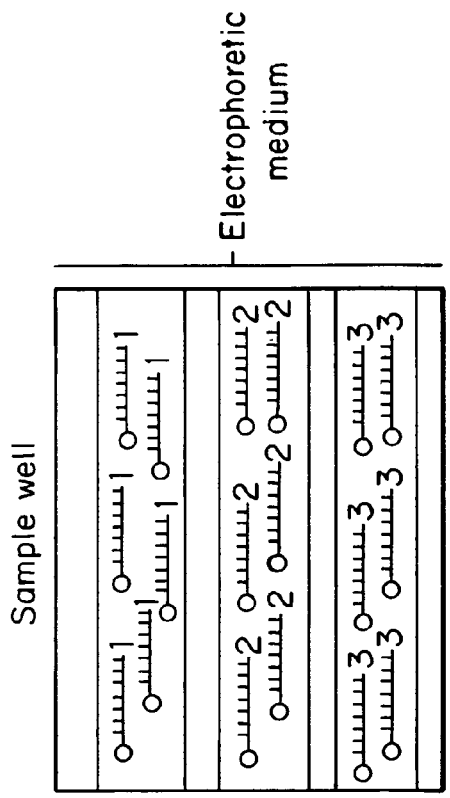
FIG. 2B is a schematic showing a gel containing a one-dimensional array of three capture probes, arranged in three layers.
Figure 2D:
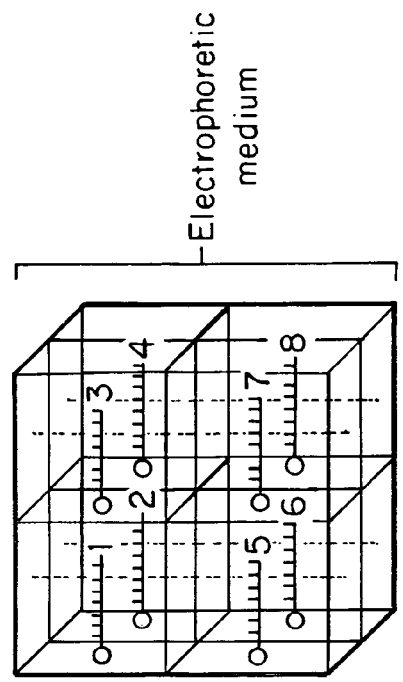
FIG. 2D is a schematic showing a gel containing a three-dimensional array of eight capture probes.
Figure 2A:
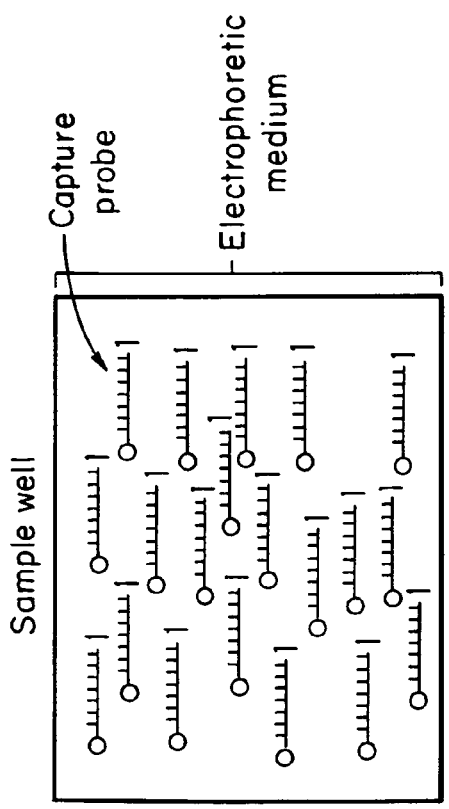
FIG. 2A is a schematic representation showing a gel modified uniformly with capture probes.

In this embodiment of the present inventions, substantially all of the medium is modified with capture probe or probes, as illustrated schematically in FIG. 2A. The choice of capture probe and electrophoresis conditions are made so that the binding between capture probe and target molecule is transient and rapidly reversible on the time scale of the electrophoretic analysis. Under these conditions, target molecules undergo many cycles of binding, release, and rebinding to the capture probes during the electrophoresis run. This reversible binding has the effect of reducing the electrophoretic mobility of the target measured relative to its mobility in the absence of capture probe. If binding to the capture probe is strong, the mobility of the target is substantially reduced. If binding to the capture probe is weak, target mobility is only slightly reduced. In this way, structurally related targets which have similar electrophoretic mobilities in the absence of capture probe, can be distinguished on the basis of their affinity for a specific capture probe. This method is especially useful for analysis of nucleic acid sequence variation as described below.

One-Dimensional Arrays for Analysis of Target Molecules

In this embodiment of the present invention, the sample containing the target molecules is electrophoresed through a series of discrete matrix layers each of which contain at least one capture probe, as illustrated schematically in FIG. 2B. For example, in a hybridization binding reaction, target nucleic acids that are complementary to the capture probe hybridize to the capture probes and are retained in the gel layer. Noncomplementary sample nucleic acids pass through the capture layer. The presence of hybrids between capture probes and complementary sample nucleic acids is detected within the capture layer by appropriate labeling strategies described herein.

There are several important advantages of this one-dimensional format. First, all of the sample passes through the capture layer, and is therefore available for hybridization. This is a major advantage over most other solid phase hybridization methods. Using high concentrations of immobilized probe, it is possible to capture all hybridizable sample nucleic acid strands in a small gel band.

Second, intact nucleic acid species that have discrete electrophoretic mobilities are not required for analysis by this method. Since hybridization and detection only require short sequence homologies, partially degraded nucleic acids will still give a signal. This attribute also increases detection sensitivity since all target nucleic acids are concentrated at a specific point in the matrix, whether they are degraded or not. In traditional zonal electrophoresis, all sample nucleic acids must migrate as a discrete band for detection.

Third, the sample volume is not important. In the present invention, all sample nucleic acids pass through the capture layer even though large samples volumes are used. This is a significant advantage over traditional zonal electrophoresis, where the sample volume needs to be as small as possible for maximum detection sensitivity and resolution.

In this embodiment, the capture layer can contain single or multiple capture probes. The use of multiple capture probes in a single layer is useful for assays where any one of a number of different organisms need to be detected. For instance, the presence of any bacteria in a blood sample to be used for transfusion is undesirable. Therefore, a general test for any bacteria might use a collection of conserved bacterial gene sequences as capture probes. Since identification of the specific bacteria is not important, the collection of probes could comprise a broad spectrum of multiple probes which helps ensure that any and all bacteria will be detected in the same capture layer.

Multiple capture layers can be also be used in this embodiment. It is straightforward to cast multiple capture layers sequentially in the same gel apparatus to create a multiplex hybridization assay. During the assay, the target sample is electrophoresed through all of the layers, and complementary sample nucleic acids are captured at each layer. The amount of hybrid in each layer directly reflects the sample composition with respect to the capture probes used.

Conditions can be identified to ensure that only properly hybridized nucleic acids will be retained in each layer. Electrophoretic hybridization with capture probes as long as 20 bases can be carried out using traditional nondenaturing gels and buffer systems at room temperature. Fully complementary hybrids of this size appear to be stable for many hours. However, additional stringency can be achieved by adding denaturants such as urea or formamide to the gel, or running the gel at elevated temperatures.

Two Dimensional Probe Arrays

Figure 2C:
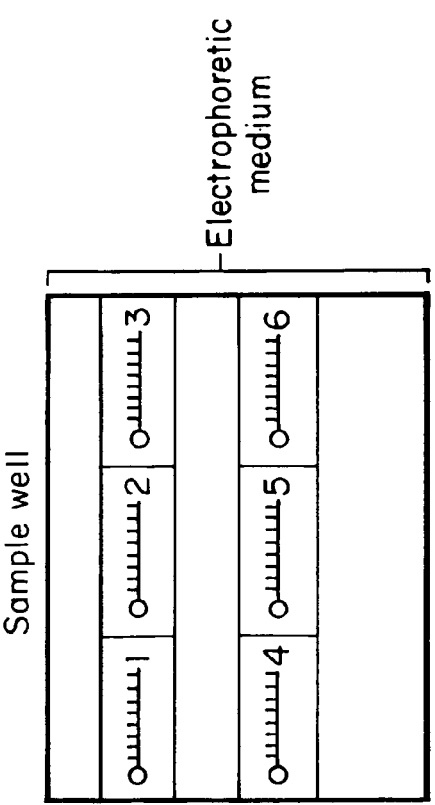
FIG. 2C is a schematic showing a gel containing a two-dimensional array of six capture probes.

One dimensional probe arrays can be used for analyses that employ limited numbers of capture probes. For analyses of larger numbers of sequences, a two-dimensional array of immobilized probes can be used. The arrays can be formed in a number of ways. Simple two-dimensional arrays can be cast, for example, in conventional slab gel devices using of multiple vertical aligned spacers, in effect creating an array of one dimensional arrays. An example of this arrangement is shown in FIG. 2C, where a single sample is loaded into the sample well, and portions of that sample will pass through six discrete capture zones.

More complex two dimensional arrays can be created in two steps, first, polymerizing the capture probe regions as an array of matrix (for example, polyacrylamide gel) dots on one plate, then "sandwiching" the dots by placing an upper gel plate over the array, and filling in the empty spaces between the probe dots with unmodified gel.

In either case, the sample is loaded as a band across the entire length of the top of the matrix. In this embodiment, the entire test sample does not contact all of the capture probes. However, for most applications where two-dimensional analysis is desirable, such as library screening or gene expression analysis, the sample nucleic acids are present at high copy numbers, and so this problem does not present a significant obstacle.

Three-Dimensional Probe Arrays

The hybridization methods described herein may also encompass three-dimensional arrays, such as may be particularly useful for multiplexed parallel assays e.g. for high throughput and/or cost-effectiveness. Such assays may be provided in the format of three-dimensional solids, as illustrated schematically in FIG. 2D, where multiple samples may be applied to a surface or face, then caused to migrate through the volume of the solid such that one or more regions of capture probe are encountered. The array may be produced such that each sample encounters the same sequence of capture probes during migration through the array, or different sequences of capture probes may be positioned for this purpose, such as to analyze different sample mixtures or to analyze differing sets of components within one or more sample mixtures.

Sample Purification/Concentration by Hybridization with Immobilized Probes

The electrophoresis methods described herein are especially useful for selectively purifying specific target molecules from a crude mixture. For example, a crude mixture or cell lysate is placed over a gel containing an immobilized capture probe. The mixture is electrophoresed through the gel. Target molecules are immobilized on the layer containing the capture probes. Non-target molecules with the same charge as the targets are attracted to the electrode of opposite electrical polarity (which will be referred to here as the "attracting electrode") and pass through the capture probe layer, eventually electrophoresing out of the gel. Non-target molecules of the opposite charge migrate out of the sample well toward the non-attracting electrode. Uncharged sample molecules remain in the sample well and do not enter the gel. After allowing sufficient electrophoresis time to be sure that all charged non-target molecules have been removed from the gel, the captured target molecules are eluted from the gel by one of two methods:

1) Continued electrophoresis under denaturing conditions (e.g., by raising the temperature of the matrix or increasing electrophoretic voltage).

2) Continued electrophoresis after chemical or photochemical cleavage of the chemical linkage between the capture probe and the matrix.

The eluted target molecules can be concentrated and recovered from the attracting electrode chamber by several methods. For instance, after electrophoresing the non-target sample molecules out of the gel, non-target molecules in the attracting electrode chamber can be flushed out with an appropriate wash solution, and the target molecules can be eluted directly into the original attracting electrode chamber. Alternatively, the electrophoresis device can have two attracting electrodes so that one is used to clear the non-target components from the sample, and the second is used to elute the target molecules. Alternatively, the electrophoresis device can be constructed with a replaceable attracting electrode chamber so that after removal of non-target components, the attracting electrode chamber can be replaced with a clean one to perform the target elution.

This embodiment is particularly well-suited for purification of specific nucleic acids from crude biological samples by hybridization methods. First, these methods result in the capture of substantially all sample nucleic acids with the desired sequence because the whole test sample must pass through the capture zone, and since the concentration of the capture probe can be made arbitrarily high, which ensures capture success.

Second, these methods result in substantial purification of target nucleic acids in one step because charged sample contaminants are eliminated during electrophoresis and uncharged contaminants are eliminated since they cannot enter the matrix.

Third, very large samples can be used. The nucleic acids undergo electrophoresis in free solution in virtually the same manner as they do in polymeric matrices. Therefore, large sample volumes can be used. The matrix layer acts like a highly selective filter to select only the desired nucleic acids from the sample.

Fourth, large volumes of very dilute samples can be concentrated quantitatively using the methods described herein.

Mutation Detection by the Rate of Sample Migration

In this embodiment, the sample and immobilized probe do not form high affinity, slowly dissociating complexes. Instead the sample and probe make transient, relatively rapidly dissociating associations during electrophoresis. The capture probe is located throughout the matrix at uniform concentration. The electrophoretic mobility of the sample nucleic acid is influenced by the extent of complementarity with the immobilized probe. Samples with complete complementarity to the probe migrate more slowly through the matrix than samples with less complementarity. Denaturant may be used in the matrix to ensure that the interactions between the target sample and capture probe are transient.

Samples can be conveniently prepared and labeled by PCR amplification with labeled nucleotide triphosphates prior to hybridization analysis.

This embodiment is particularly useful for typing a series of defined mutation sites within an amplifiable gene fragment. A matrix with many physically separate vertical lanes is used. Each lane contains a different immobilized probe. Each probe contains the wild-type sequence of a specific gene region to be tested. In a particular embodiment, all regions of the gene to be tested by the matrix can be amplified as a single fragment.

For example, to perform this analysis, a labeled single-stranded nucleic acid product is prepared from the sample to be tested, using asymmetric PCR with fluorescein-labeled nucleotides. The fluorescein product is mixed with a rhodamine-labeled internal standard PCR product having the non-mutated (wild type, or normal) sequence, and loaded evenly over the top of the gel. After electrophoresis, a color image of the gel is captured, and the sample and internal standard are identified (test sample: yellow-green, internal standard: red). If the test sample migrates faster than internal control in a given lane, the test sample is mutant at some position within the sequence covered by the immobilized probe. For big genes, a set of several gels would be required to cover all the mutable sequence positions. (See FIG. 3).

Detection Schemes

Detection of the specific binding reaction, e.g., detection of the immobilized target molecule bound to the capture probe, can be accomplished in a number of different ways. For example, the test molecule can be detectably labelled prior to the binding reaction. Suitable labels for direct target labelling can be intensely absorbing (e.g., brightly colored), radioactive, fluorescent, phosphorescent, chemiluminescent or catalytic. Direct target labeling of nucleic acid samples using modified nucleotides can be accomplished by a number of enzymatic methods well known to those practiced in the art (reviewed in Sambrook, et al., "Molecular Cloning: A Laboratory Manual", 2nd edition, Cold Spring Harbor Press, Cold Spring Harbor, N.Y. 1989).

Alternatively, the target molecule can be labeled indirectly using a ligand which can be recognized by a second specific binding entity which is either labeled itself or can produce a detectable signal. An example of such an indirect system is labeling using biotinylated nucleotides. In this system, the sample is labeled enzymatically using standard nucleic acid labeling techniques and biotinylated nucleotides. The resulting biotin-modified nucleic acids can be detected by the biotin-specific binding of streptavidin or avidin proteins molecules. The streptavidin or avidin molecules can be conjugated to fluorescent labels, such as fluorescein or reporter enzymes, such as alkaline phosphatase or horseradish peroxidase, which can be used to produce chemiluminescent or calorimetric signals with appropriate substrates (for review see Keller and Manak, "DNA Probes", 2nd ed., Macmillan Publishers, London, 1993; Pershing, et al., eds "Diagnostic Molecular Microbiology: Principles and Applications", American Society for Microbiology, Washington, D.C., 1993). Another useful detection system is the digoxigenin system which uses an anti-digoxigenin antibody, conjugated to alkaline phosphatase, which recognizes digoxigenin-dUTP incorporated into nucleic acids. (CURRENT PROTOCOLS IN MOLECULAR BIOLOGY, ed. Ausubel, F. M., vol.1, §§ 3.18.1 to 3.19.6, 1995).

Detectably labeled hybridization probes can also be used as indirect target labels. For example, target nucleic acids can be indirectly labeled prior to electrophoresis by hybridization with a detectably labeled probe, hereafter termed a "sandwich" probe. The sandwich probe is designed to hybridize with a region of the target which does not overlap the region recognized by the capture probe. The sandwich probe is designed to remain associated with the target during electrophoresis, and cannot bind directly to the capture probe.

Sandwich probes can also be used to label target molecules after electrophoretic capture. In this labeling strategy, the unlabeled target is electrophoresed and hybridized to the capture probes first. Then, the sandwich probe is electrophoresed through the capture layer. In effect, the captured target now acts as a new "capture" probe for the sandwich probe. The captured target sandwich probe complex can now be detected through the sandwich probe label.

Blotting techniques can also be adapted for detection of target bound capture probes. For example, a detection surface is juxtaposed to the separation medium having bound sample components, and the sample components then migrate to the detection surface, optionally assisted by, e.g., chemical means such as solvent or reagent changes, where the transferred sample components are detected by known means such as optical detection of intercalating dyes, or by detection of radioactivity from hybridized radioactive species, or other known means.

A variety of optical techniques can be used to detect the presence of sample components bound to the capture probes. For example, if the capture probes are arranged in a linear array, the position and intensity of each signal may be measured by mechanically or optically scanning a single detector along the array of detectable signals. Alternately, a linear array of detectable signals may be detected by a linear array detector, such as by juxtaposition of the array detector to the array of detectable signals or by optically imaging all or part of the signal array onto the array detector.

When the capture probes with detectable signals are arranged as a two-dimensional array, a number of detection schemes may be employed. A single detector may be used to measure the signal at each point by mechanical or optical scanning, or by any combination. Alternately, a linear optical detection array may be used to detect a set of signals by juxtaposition or optical imaging, and multiple sets of such signals may be detected by mechanically or optically scanning the signal array or detector. Alternately, the two-dimensional array of capture probes may be optically detected in whole or in part by a two-dimensional optical area detector by juxtaposition to, or optical imaging of, the array of optical signals from the immobilized capture probes.

When the capture probes are arranged as a three-dimensional array, detection of individual signals may be arranged by the above techniques, optionally assisted by first physically taking one or more sub-sections of the array. Alternately, optical schemes such as confocal microscopic techniques may be employed whereby one or a number of detectable signals are imaged and detected with minimal interference from others, and other signals are subsequently detected after optical adjustment.

Matrix Formats and Methods of Producing Matrices

Matrices may be configured in a variety of formats. For example, a linear gel may be formed by techniques including formation within a linear support, such as a trough or tube, where the gel is formed by polymerization within the support, or alternately by subdividing a two-dimensional gel into a number of strips, including by partitions or formation in channels. With the trough, strip or channel formats, quantities of one or more copolymerizable capture probes can be added to the gel material, optionally in spatially defined positions, such as by spatially positioned dropper techniques, either before or during gel polymerization to provide one or more capture probes within the polymerized gel. With the tube format, a sequence of gel monomers and mixtures of gel monomers and polymerizable capture probes may be introduced into the tube sequentially such as to provide a spatially distinguished set of components and concentrations which are then polymerized in situ to preserve the components' spatial relationships. To preserve the integrity of the gel during polymerization induced shrinkage, the tube walls can be made of elastic material which laterally contracts during shrinkage of the gel. Alternatively, progressive polymerization may be induced from one end of the tube while adding more liquid material to the other end to compensate for shrinkage. Such progressive polymerization may be induced by means including diffusion of a polymerization catalytic agent, or by progressive application of polymerization inducing electromagnetic or other radiation from one end of the tube to the other, such as by movement of, or progressive exposure to, the radiation source. Alternately, a linear format gel may be produced by taking a linear slice from a two-dimensional gel, or a linear core from a three-dimensional gel, produced as described below.

A two-dimensional gel may be formed by techniques including formation on a surface of a support, or formation between two support surfaces. A layer of gel monomer is applied and quantities of copolymerizable capture probes may be applied to the layer, optionally in a spatially significant manner, before or during polymerization, which are then polymerized in situ to preserve their spatial positions in the gel. Application of quantities of polymerizable capture probes may be effected by known means including positionally programmable dropper techniques. Gel shrinkage during polymerization may be adjusted for by means including permitting contraction of the gap between support surfaces and by permitting lateral contraction with more material added from the side to compensate. A two-dimensional gel may be subdivided into a number of strips, by the use of partitions before, during or after gel formation, or by formation in channels, or by being sliced into narrower sections after formation.

Three-dimensional gels may be formed by a number of techniques. Multiple linear strips or two-dimensional layers may be repetitively constructed as above, each optionally containing localized capture probes, with each strip or layer being polymerized onto an underlying layer such that a three-dimensional volume results. Alternately, a number of two-dimensional gels, optionally with capture probes localized in place, may be formed as above and assembled together to provide a three-dimensional structure.

Manufacturing Apparatus.

A variety of apparatus can be used to produce the matrices described herein. For example, an apparatus can produce matrices in cores by us of a progressive fill/shrinkage apparatus or can core matrices from solids. Matrices can be formed on solid surfaces, between plates or by using formed plates to make physical channels.

The present invention is further exemplified by the following examples, which are not to be construed as limiting in any way.

EXAMPLE 1

One-Dimensional Electrophoretic Hybridization

The gel was polymerized in three sections. The bottom layer contained 20% acrylamide (29:1 wt ratio acrylamide:bis-acrylamide) in 0.5×TBE (45 mM Tris-borate pH 8.3, 1 mM EDTA). The lower gel was 0.15 mm thick, approximately 5 cm tall and 8 cm wide. In all cases, polymerization was accomplished by adding 2 µl TEMED, and 7 µl 10% (wt/vol in water) ammonium persulfate per milliliter of gel solution. After the bottom layer polymerized, three capture layers 0.5 cm tall by 2 cm wide by 0.15 mm thick were polymerized using 20, 10, or 4% acrylamide (all 29:1 monomer:bis), in the presence of 10 µM single-stranded synthetic oligonucleotide capture probe (5'-ttt ttt ttt acg cag cga cga gca cga gag-3') (SEQ ID NO: 1) and 0.5×TBE buffer. The 5' phosphate termini of the capture probes were covalently modified with N-(6-aminohexyl)methacrylamide groups. The hexylmethacrylamide groups were added during automated DNA synthesis using a hexylmethacryamide phosphoramidite (Glen Research, Sterling, Va.). Using this attachment method, the probes copolymerize with the gel matrix during polymerization of the capture layers, because of the presence of the 5' terminal methacrylamide groups. The side boundaries of the capture layers were formed by inserting thin 0.15 cm thick spacers down from the top of the gel plate sandwich until they contacted top surface of lower 20% gel. After polymerization of the capture layers, the top layer of the gel was poured using 10% acrylamide 0.5×TBE, and a comb was inserted to form sample wells.

Figures 3A, 3B:
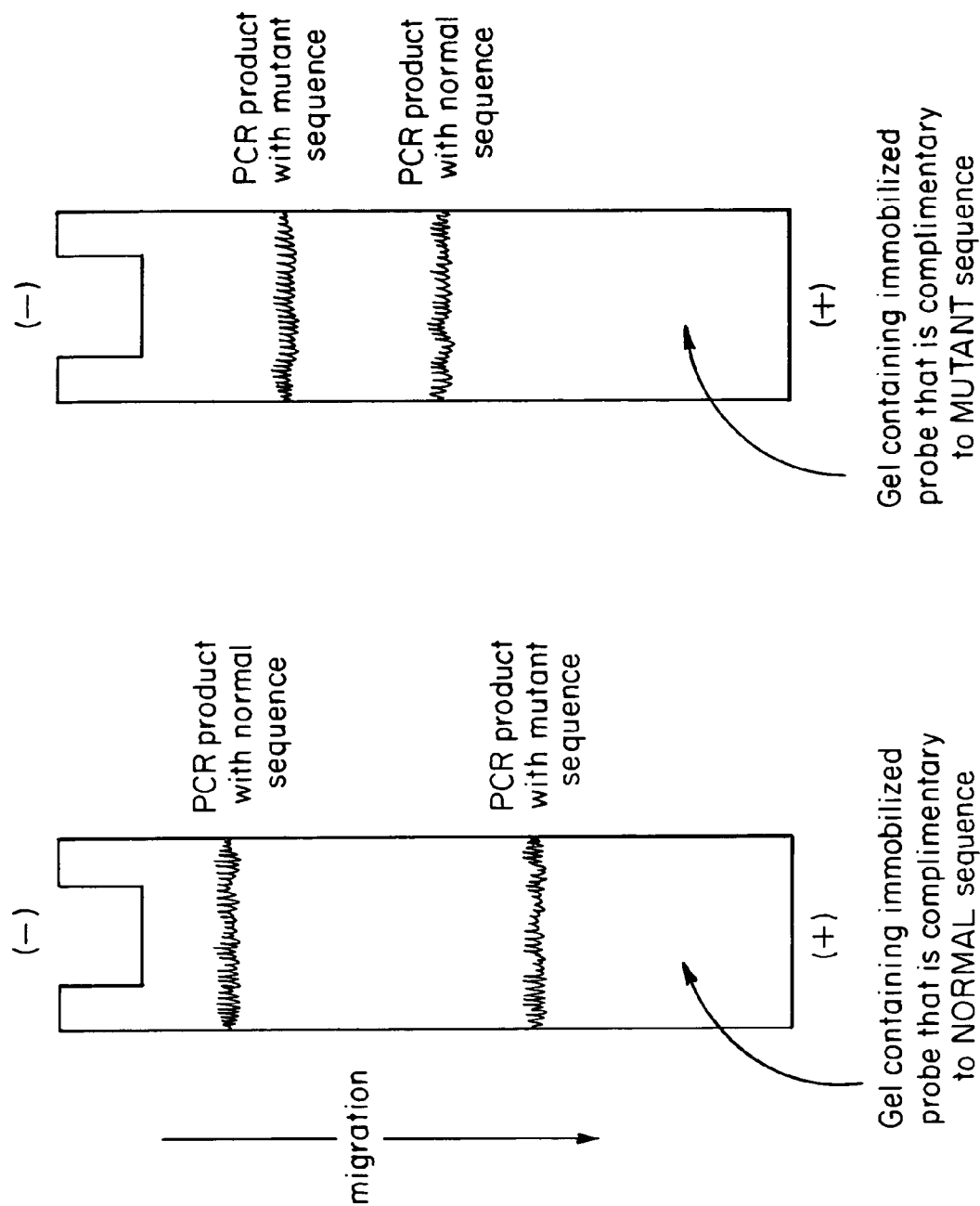
FIGS. 3A and B are a graphic depictions of the principle of electrophoretic analysis of mutant nucleic acid sequences.
FIG. 3B depicts a gel containing immobilized probes that are complementary to mutant sequences.
Figure 4:
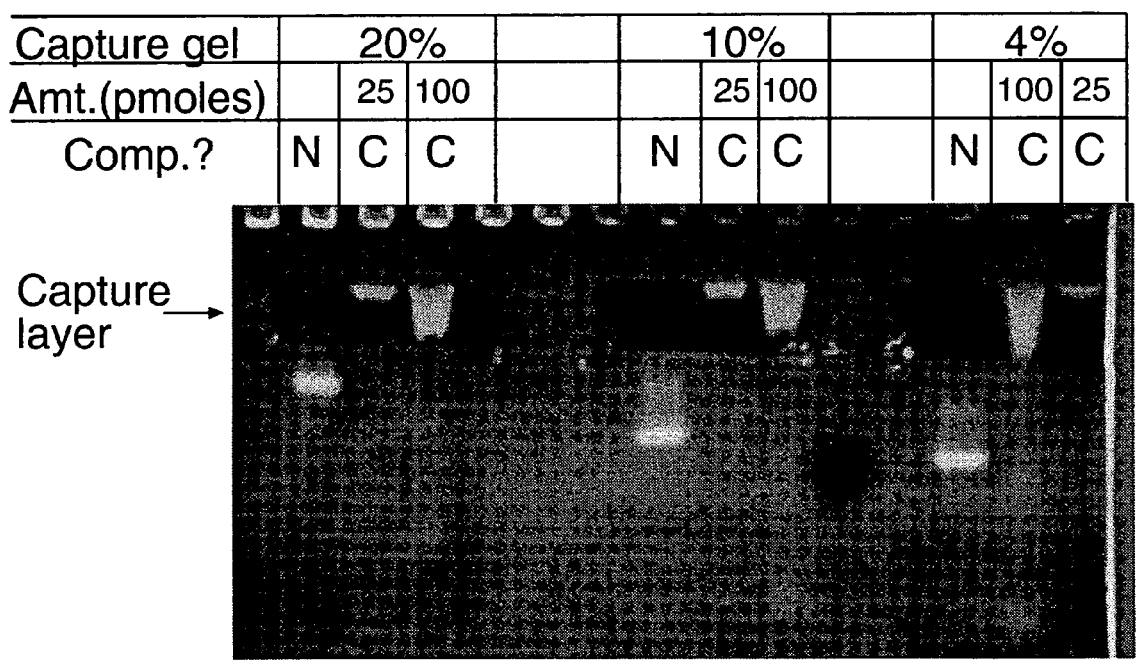
FIG. 4 is a photograph depicting hybridization of a nucleic acid to gel-immobilized probes.

Electrophoretic hybridization was carried out by loading 25 and 100 picomole samples (See FIG. 4) of a complementary fluorescein-labeled single-stranded oligonucleotide (5'-fluorescein-ct ctc gtg ctc gtc gct gcg t-3') (SEQ ID NO:2) were electrophoresed through each capture layer (see "Comp.?" label at top of gel, "C" lanes in FIG. 3). As a control, 100 picomole samples of a noncomplementary fluorescein-labeled oligonucleotide (5'-fluorescein-at tac gtt gat att gct gat ta-3') (SEQ ID NO:3) were also electrophoresed through each capture zone. Electrophoresis was carried out at 7 V/cm for two hours at room temperature, after which the gel was photographed under UV illumination.

The results shown in FIG. 3 show that the complementary samples ("C" lanes) were completely immobilized on the capture layer, while non-complementary DNA ("N" lanes) of the same length was not retained in the capture layers. This suggests that complementary base pairing between the complementary samples and the capture probe is responsible for the immobilization of the fluorescein-labeled complementary samples in the capture layer.

EXAMPLE 2

Cyanuric Chloride Methods for Preparation of Polysaccharide-Based Electrophoresis Media Containing Immobilized Nucleic Acid Probes Protocol 1: Activated Carrier Approach The following example utilizes the carrier activation methods of Biagioni et al. (*Anal. Biochem.*, vol. 89, pp. 616-619, 1978) and Smith and Lenhoff (*Anal. Biochem.*, vol. 61, 392-415). Although developed for use with cellulose supports, the method is generally applicable to any insoluble supports containing hydroxyl groups. The supports of choice for this method include starch, agarose, dextrans, and cellulose.

Most agarose (for example, Sea Plaque or Sea Kem, FMC Bioproducts) and starch preparations (Catalog numbers S5651 and S4501, Sigma Chemical) for electrophoresis are supplied as powders that are insoluble in water and organic solvent. The powder is washed extensively with distilled water on a Buchner funnel. The washed powder is suspended in 3M sodium hydroxide for 15 minutes are room temperature, after which the solution is removed by filtration. The damp alkaline powder is added with stirring to a 5% solution of cyanuric chloride dissolved in a 1:1 (vol/vol) mixture of dioxane and xylene. Twenty milliliters of 5% cyanuric chloride solution are used per gram (dry weight) of carrier. After stirring for 30 minutes at room temperature, the carrier is washed extensively with each of the following solvents: dioxane, acetic acid/dioxane/water (1:2:1, w/w/w), and acetone. The carrier is dried under vacuum and stored dry. Oligonucleotide probes containing 5' or 3' primary amine termini are attached by resuspending the activated carrier in 0.1M sodium borate buffer pH 8.3 containing the desired probe or probes. Preferably the probe concentration is greater than 500 nanomoles amine-terminal oligonucleotide per gram of dry activated carrier. The attachment reaction is carried out at room temperature for 12 hours with vigorous stirring or shaking. Following attachment, ethanolamine-HCl (pH 8.3) is added to a final concentration of 1M and the carrier is shaken for an additional 12 hours. The modified carrier is washed extensively with buffer and stored as a suspension, preferably in the buffer to be used for electrophoresis.

To cast capture layers in agarose and starch gels, the probe-modified powdered carrier can be cast into gels using the same methods as for unmodified carriers, as describe in standard references such as Sambrook, et al., "Molecular Cloning: A Laboratory Manual", 2nd edition, Cold Spring Harbor Press, Cold Spring Harbor, N.Y. 1989). Briefly, probe-modified powdered carrier is suspended in gel buffer, melted by heating, poured into a gel mold, and allowed to cool. IN most cases, the gel mold will be a slot or hole cut into a gel prepared from underivatized carrier. This method provides discrete boundaries to the capture layer, and reduces the volume of modified gel which must be used in the experiment.

Protocol 2: Activated Probe Approach

This protocol is useful for powdered carriers and soluble polysaccharide polymers such as hydroxyethyl cellulose. In principle any separation medium having hydroxl or primary amine group, soluble or insoluble can be modified using this approach. Soluble polymers are becoming increasingly important as replaceable separation media for capillary electrophoresis applications as described by Quesada (*Current Opinion in Biotechnology*, vol. 8, pp. 82-93, 1997).

The probe activation protocol is modified from Van Ness et al. (*Nucleic Acids Res*. vol. 19, pp. 3345-3350, 1991). Reactions contain 200 µm 5'- or 3'-amino-terminal probe, 0.1 M sodium borate buffer (pH8.3) (SBB), 1 mM cyanuric chloride (Aldrich), 10% acetonitrile (v/v) (Aldrich). Reactions are carried out for 1-2 hours at room temperature with vigorous shaking. Unreacted cyanuric chloride is removed by three cycles of centrifugal ultrafiltration and resuspension in 0.1M SBB using a Microcon 3 (3000 dalton cutoff, Amicon). Activated probes are stored at 4° C., and can be used with no detectable loss of activity for up to 2 months.

Attachment to insoluble (powdered) media such as starch and agarose is performed by washing the powdered media extensively with distilled water and then with 0.1 M SBB pH 8.3. The media is suspended in 0.1 M SBB and shaken overnight with cyanuric chloride-activated probe at room temperature. Preferably, the concentration of activated probe is present is greater than 500 nanomoles per gram of polymer. Following the reaction, the modified medium is washed extensively with 0.1 M SBB followed by electrophoresis buffer. Gel capture layers are cast as described in the previous protocol.

Soluble polymer media, such as modified cellulose, is dissolved in water and dialyzed against 0.1 M SBB. Following dialysis, the polymer is mixed with activated probe and shaken vigorously overnight at room temperature. Preferably, the amount of activated probe is greater than 500 nanomoles per gram of polymer. Following the attachment reaction, unreacted probe is removed by dialysis or centrifugal ultrafiltration (Centricon or Microcon 50 filters, for media greater than 50,000 dalton molecular weight, Amicon). Alternatively, unbound probes are removed by preelectrophoresing the media prior to sample loading.

EXAMPLE 3

DNA Aptamer Gel for Determining the Presence of a Specific Protein (Human Thrombin)

This example illustrates the use of a nucleic acid aptamer to analyze samples for the presence of a specific protein, in this case human thrombin, a protease important in the blood clotting cascade. The gel is cast in three sections as described in Example 1 with the exceptions that 1) the total gel concentration in all layers is lowered to 5% (29:1 weight ratio monomer:bisacylamide), and 2) that the gel is cast and run in 20 mM Tris-acetate, pH 8.0, 140 mM NaCl, 5 mM KCl, 1 mM $MgCl_2$, 1 mM CaCl2. The capture layer contains the thrombin-binding DNA aptamer identified by Block, et al., (Nature 355:564-566 (1992)) attached to the hexylacrylamide group (Glen Research, Sterling, Va.) via polyethylene glycol spacer groups ("Spacer9, Spacer Phosphoramidite 9, catalog 10-1909-90, Glen Research, Sterling, Va.) as follows:
5'-hexylacrylamide-(Spacer9)$_6$-GGGTTGGTGTGGTTGG-3' (SEQ ID NO:4).

The aptamer is immobilized in the capture layer at a concentration between 10 and 100 µM (concentrations of strands). Electrophoresis is carried out in a cooled apparatus with buffer recirculation between the buffer compartments. Non-denatured samples of human serum are loaded on the gel and electrophoresed toward the positive electrode at 2-5 V/cm, keeping the gel temperature between 25° C. and 30° C. Electrophoresis is carried long enough to permit all non-thrombin proteins to pass through the capture layer. T\Following electrophoresis, the gel is stained for detection of protein using colored (coomassie blue or silver stain, products 161-0499 and 161-0400, respectively, Bio Rad Laboratories, Richmond, Calif.) or fluorescent (SYPRO orange dye, product S-6650, Molecular Probes, Eugen, Oreg.) reagents. The presence of protein in the capture layer indicates the presence of thrombin in the sample.

EXAMPLE 4

Capture Gel for Assaying Proteins Capable of Binding to Gene Regulatory Sequences This sample illustrates the use of a double-stranded DNA capture probe to analyze samples for the presence of proteins, which would bind specifically to a gene regulatory sequence, in this case the lactose operator sequence (Gilbert and Maxam, Proc. Natl. Acad. Sci. USA, 70:3581-3584 (1973)). The gel is cast in three sections as described in Example 1 with the exceptions that 1) the total gel concentration in all layers is lowered to 5% (29:1 weight ration monomer: bisacrylamide), and 2) that the gel is cast and run in 45 mM Tris-borate, pH 8.3, 1.5 mM EDTA.

The capture layer contains a double stranded oligonucleotide formed by hybridizing the following two synthetic single-stranded oligonucleotides:
5'-hexylacrylamide-(Spacer9)$_6$-GAATTCAAATTGT-GAGCGGATAACAATTTGAATT-3' (SEQ ID NO:5)
5'-GAATTCAAATTGTTATCCGCTCA-CAATTTGAATTC-3 (SEO ID NO:6)
where the under lined sequences indicated the lac operator sequence (Gilbert and Maxam, Proc. Natl. Acad. Sci. USA, 70:3581-3584 (1973)), the hexylacrylamide group is from Glen Research (Sterling Va.), and "Spacer9" indicates a polyethylene glycol spacer groups (Spacer PHosphoramidite 9, catalog 10-1909-90, Glen Research, Sterling, Va.). To prepare the double-stranded capture probe, the two oligonucleotides are mixed in equimolar ratio, hybridized by heating the mixture to 95° C. (in 50 mM Tris-HCl, pH 8.3, 1 mM EDTA, 1 M NaCl) and cooling to 25° C. over a period of 3 hours. After hybridization, the double stranded capture probe is recovered from the hybridization mixture by preparative nondenaturing polyacrylamide gel electrophoresis.

The double-stranded capture probe is present in the capture layer at a concentration of between 10 and 100 µM (concentration of the duplex). Electrophoresis is carried out in a cooled apparatus with buffer recirculation between the buffer compartments. Nondenatured samples, possibly containing lac repressor protein, are loaded on the gel and electrophoresed toward the negative electrode at 2-5 V/cm, keeping the gel temperature between 25° C. and 30° C. Electrophoresis is carried long enough to permit all proteins, except those expected to be captured, to pass through the capture layer. Following electrophoresis, the gel is stained for detection of protein using colored (coomassie blue or silver stain, products 161-0449 and 161-0400, respectively, Bio-Rad Laboratories, Richmond, Calif.) or fluorescent (SYPRO orange die, product S-6650, Molecular Probes, Eugene, Oreg.) reagents. The presence of protein in the capture layer indicates the presence of lac operator-binding proteins in the sample.

The specificity of the binding reaction can be determined by running a duplicate sample in another gel lane where the capture layer contains a capture probe which is unrelated in sequence to the lac operator. If the sample shows binding to the lac operator probe but not the unrelated probe, then the binding activity is specific for the lac operator probe.

EXAMPLE 5

Preparation of Soluble Polymer Matrix Containing Capture Probes Suitable for Use in Capillary Electrophoresis Experiments All procedures are carried out at room temperature (approximately 22° C.). A three milliliter solution containing 10 µM 5'-hexylacrylamide synthetic oligonucleotide capture probe, 6% (weight/volume) monomer acrylamide, and 0.5× TBE buffer (45 mM Tris-borate pH 8.3, 1 mM EDTA) is prepared. The hexylacrylamide-derivatized capture probe is described in Example 1 is used (5'-hexylacrylamide-ttt ttt ttt acg cag cga cga gca cga gag-3') (SEQ ID NO:7). Nitrogen gas is bubbled through the solution for 30 minutes to remove dissolved oxygen. Deoxygenation and subsequent polymerization are carried out in a nitrogen atmosphere using a plastic glove bag. Polymerization is initiated by adding 3-10 µl of freshly prepared 10% ammonium persulfate and 1-3 µl of TEMED. The mixture is stirred slowly on a magnetic stirrer during catalyst addition and polymerization. The solution will become noticeably viscous 30 minutes after catalyst addition and polymerization is continued for an additional hour. The polymer solution is then transfered to a dialysis bag (molecular weight cut off: 50,000 daltons) and electrophoresed in an horizontal agarose gel electrophoresis apparatus at 1 V/cm in 0.5×TBE buffer for 12 hours to remove capture probe which was not copolymerized into acrylamide polymer.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of detecting the presence or absence of one or more target molecules in a test sample, wherein the one or more target molecules has a defined mobility in an appropriate electrophoretic medium when the medium is exposed to an electric field and the target molecule can form binding complexes with capture probes, comprising the steps of:
   a) copolymerizing one or more capture probes with a material capable of forming a matrix suitable for electrophoresis to form an electrophoretic medium containing immobilized capture probes covalently attached to the electrophoretic medium, wherein said one or more capture probes are modified with a 5'-acrylamide moiety and are selected from the group consisting of a nucleic acid, modified nucleic acid and a nucleic acid analog, and wherein said one or more capture probes are immobilized in a two dimensional array within the electrophoretic medium;
   b) introducing a test sample into the electrophoretic medium;
   c) subjecting the electrophoretic medium to an electric field resulting in the electrophoretic migration of the test sample into the region or regions of the electrophoretic medium containing immobilized capture probes, under conditions suitable for the target molecules to bind to the immobilized probes; and
   d) detecting the presence, or absence of target molecules or target molecule/capture probe complexes immobilized in the medium,
   thereby detecting the presence or absence of one or more target molecules in the test sample.

2. The method of claim 1, wherein the medium is a gel formed from at least one type of polymer.

3. The method of claim 2, wherein the electrophoretic medium is formed using a polymer of polyacrylamide.

4. The method of claim 1, wherein the capture probes are attached to the acrylamide via a polyethylene glycol spacer group.

5. The method of claim 1, wherein the capture probes are immobilized in a discrete region or regions of the electrophoretic medium.

6. The method of claim 1, wherein the electrophoretic medium contains multiple classes of capture probes, and wherein each class of capture probes is immobilized in a discrete region of the electrophoretic medium.

7. The method of claim 1, wherein the target molecule is selected from the group consisting of: nucleic acids, modified nucleic acids, nucleic acid analogs, proteins, carbohydrates, polysaccharides and small organic molecules.

8. The method of claim 1, wherein the target molecule is either a single-stranded or double-stranded nucleic acid molecule.

9. The method of claim 1, wherein the capture probe is about 5-50 nucleotides in length.

10. A method for purifying or concentrating target molecules from a complex test sample, comprising:
    a) copolymerizing one or more capture probes modified with a 5'-acrylamide moiety and selected from the group consisting of a nucleic acid, modified nucleic acid and a nucleic acid analog with a material capable of forming a matrix suitable for electrophoresis to form an electrophoretic medium containing immobilized capture probes covalently attached to the electrophoretic medium, wherein said one or more capture probes are immobilized in a two dimensional array within the electrophoretic medium;

b) introducing a test sample into the electrophoretic medium;

c) subjecting the electrophoretic medium to an electric field resulting in the electrophoretic migration of the test sample through the medium, under conditions and time sufficient for the target molecules in the test sample to specifically bind to the capture probes, thereby forming target molecule/capture probe complexes, and for non-target molecules to migrate through and elute from the medium, wherein only target molecules bind to the capture probes and are immobilized in the medium;

d) treating the electrophoretic medium to release at least one of the following:
  i) the one or more capture probes,
  ii) the target molecules, or
  iii) the target/capture probe binding complexes; and e) eluting the target molecules or target/capture probe complexes from the medium, whereby the released and eluted target molecules are substantially pure.

11. The method of claim 10, wherein the releasing treatment is accomplished by raising the temperature of the medium to a temperature sufficient to denature the target/capture probe complexes.

12. The method of claim 10, wherein the releasing treatment is accomplished by chemical cleavage of the chemical linkage which immobilizes the capture probe within the medium, and the released target molecule/capture probe complex is eluted from the medium.

13. The method of claim 10, wherein the releasing treatment is accomplished by photochemical cleavage of the chemical linkage which immobilizes the capture probe within the medium, and the released target molecule/capture probe complex is eluted from the medium.

14. The method of claim 10, wherein the releasing treatment is accomplished by increasing the electrophoretic field strength.

15. The method of claim 10, wherein the target molecule is selected from the group consisting of: nucleic acids, modified nucleic acids, nucleic acid analogs, proteins, carbohydrates, polysaccharides and small organic molecules.

16. The method of claim 10, wherein the capture probe is about 5-50 nucleotides in length.

17. A method of detecting one or more target molecules in a test sample, comprising the steps of:
  a) copolymerizing one or more nucleic acid aptamer capture probes modified with a 5'-acrylamide moiety with a material capable of forming a matrix suitable for electrophoresis to form an electrophoretic medium containing at least one immobilized nucleic acid aptamer capture probe covalently attached to the electrophoretic medium, wherein the aptamer capture probe is a thrombin-binding DNA aptamer;
  b) introducing a test sample into the electrophoretic medium;
  c) subjecting the electrophoretic medium to an electric field resulting in the electrophoretic migration of the test sample into the electrophoretic medium under conditions suitable for the target molecules to bind to the at least one immobilized aptamer capture probe, wherein the target molecule is human thrombin and is SEQ ID No.1; and
  d) detecting the presence or absence of target molecule/aptamer capture probe complexes immobilized in the medium,
thereby detecting the presence or absence of one or more target molecules in the test sample.

18. The method of claim 17, wherein the concentration of the aptamer capture probe immobilized in the electrophoretic medium is from about 10 to about 100 µM.

19. The method of claim 17, wherein the aptamer capture probe is attached to the acrylamide moiety via a polyethylene glycol spacer group.

20. A method of detecting one or more target molecules in a test sample, comprising the steps of:
  a) copolymerizing one or more nucleic acid aptamer capture probes modified with a 5'-acrylamide moiety with a material capable of forming a matrix suitable for electrophoresis to form an electrophoretic medium containing at least one immobilized nucleic acid aptamer capture probe covalently attached to the electrophoretic medium;
  b) introducing a test sample into the electrophoretic medium:
  c) subjecting the electrophoretic medium to an electric field resulting in the electrophoretic migration of the test sample into the electrophoretic medium under conditions suitable for the target molecules to bind to the at least one immobilized aptamer capture probe, wherein the target molecule is selected from the group consisting of: SEQ ID No.2 and SEQ ID No.3; and
  d) detecting the presence or absence of target molecule/aptamer capture probe complexes immobilized in the medium,
thereby detecting the presence or absence of one or more target molecules in the test sample.

21. A method for purifying molecules in a complex test sample comprising target molecules and non-target molecules, comprising:
  a) copolymerizing one or more capture probes modified with a 5'-acrylamide moiety and selected from the group consisting of a nucleic acid, modified nucleic acid and a nucleic acid analog with a material capable of forming a matrix suitable for electrophoresis to form an electrophoretic medium containing immobilized capture probes covalently attached to the electrophoretic medium, wherein said one or more capture probes are immobilized in a two dimensional array within the electrophoretic medium;
  b) introducing a test sample into the electrophoretic medium;
  c) subjecting the electrophoretic medium to an electric field resulting in the electrophoretic migration of the test sample through the medium, under conditions and time sufficient for the target molecules in the test sample to specifically bind to the capture probes, thereby forming target molecule/capture probe complexes and allowing non-target molecules to migrate through and elute from the medium, wherein only target molecules bind to the capture probes and are immobilized in the medium,
thereby subtracting out the target molecule from the sample preparation and purifying molecules in the complex test sample.

22. A method of detecting the presence or absence of one or more target molecules in a test sample, wherein the one or more target molecules have a defined mobility in an appropriate electrophoretic medium when the medium is exposed to an electric field and the one or more target molecules can form binding complexes with capture probes, comprising the steps of:
  a) copolymerizing one or more capture probes with a material capable of forming a matrix suitable for electrophoresis, wherein said copolymerization forms an electrophoretic medium containing immobilized capture probes covalently attached to the electrophoretic medium, and wherein said one or more capture probes are modified with a monomer capable of forming a matrix suitable for electrophoresis, and wherein said capture probes are selected from the group consisting of a nucleic acid, modified nucleic acid and a nucleic acid analog, and wherein one or more capture probes are immobilized in a two dimensional array within the electrophoretic medium, b) introducing a test sample into the electrophoretic medium;

c) subjecting the electrophoretic medium to an electric field resulting in the electrophoretic migration of the test sample into the region or regions of the electrophoretic medium containing immobilized capture probes, under conditions suitable for the target molecules to bind to the immobilized probes; and d) detecting the presence or absence of target molecules or target molecule/capture probe complexes immobilized in the medium, thereby detecting the presence or absence of one or more target molecules in the test sample.

23. The method of claim 22, wherein the medium is formed from at least one type of polymer.

24. The method of claim 23, wherein the electrophoretic medium is formed using at least one class of polymers selected from the group consisting of: polyacrylamide, agarose and starch.

25. The method of claim 22, wherein the capture probes are immobilized in a discrete region or regions of the electrophoretic medium.

26. The method of claim 22, wherein the electrophoretic medium contains multiple classes of capture probes, and wherein each class of capture probes is immobilized in a discrete region of the electrophoretic medium.

27. The method of claim 22, wherein the target molecule is selected from the group consisting of: nucleic acids, modified nucleic acids, nucleic acid analogs, proteins, carbohydrates, polysaccharides and small organic molecules.

28. The method of claim 22, wherein the target molecule is either a single-stranded or double-stranded nucleic acid molecule.

29. The method of claim 22, wherein the capture probe is about 5-50 nucleotides in length.

30. A method for purifying or concentrating target molecules from a complex test sample, comprising:

a) copolymerizing one or more capture probes with a material capable of forming a matrix suitable for electrophoresis, wherein said copolymerization forms an electrophoretic medium containing immobilized capture probes covalently attached to the electrophoretic medium, and wherein said one or more capture probes are modified with a monomer capable of forming a matrix suitable for electrophoresis, and wherein said capture probes are selected from the group consisting of a nucleic acid, modified nucleic acid and a nucleic acid analog, and wherein one or more capture probes are immobilized in a two dimensional array within the electrophoretic medium, b) introducing a test sample into the electrophoretic medium;

c) subjecting the electrophoretic medium to an electric field resulting in the electrophoretic migration of the test sample through the medium, under conditions and time sufficient for the target molecules in the test sample to specifically bind to the capture probes, thereby forming target molecule/capture probe complexes, and for non-target molecules to migrate through and elute from the medium, wherein only target molecules bind to the capture probes and are immobilized in the medium;

d) treating the electrophoretic medium to release at least one of the following:
  i) the one or more capture probe,
  ii) the target molecules, or
  iii) the target/capture probe binding-complexes; and e) eluting the target molecules or target/capture probe complexes from the medium, whereby the released and eluted target molecules are substantially pure.

31. The method of claim 30, wherein the releasing treatment is accomplished by raising the temperature of the medium to a temperature sufficient to denature the target/capture probe complexes.

32. The method of claim 30, wherein the releasing treatment is accomplished by chemical cleavage of the chemical linkage which immobilizes the capture probe within the medium, and the released target molecule/capture probe complex is eluted from the medium.

33. The method of claim 30, wherein the releasing treatment is accomplished by photochemical cleavage of the chemical linkage which immobilizes the capture probe within the medium, and the released target molecule/capture probe complex is eluted from the medium.

34. The method of claim 30, wherein the releasing treatment is accomplished by increasing the electrophoretic field strength to a level sufficient to disrupt target/capture probe complexes.

35. The method of claim 30, wherein the target molecule is selected from the group consisting of: nucleic acids, modified nucleic acids, nucleic acid analogs, proteins, carbohydrates, polysaccharides and small organic molecules.

36. The method of claim 30, wherein the capture probe is about 5-50 nucleotides in length.

37. A method of detecting one or more target molecules in a test sample, comprising the steps of:

a) copolymerizing one or more aptamer capture probes with a material capable of forming a matrix suitable for electrophoresis, wherein said copolymerization forms an electrophoretic medium containing immobilized aptamer capture probes covalently attached to the electrophoretic medium, and wherein said one or more aptamer capture probes are modified with a monomer capable of forming a matrix suitable for electrophoresis, and wherein the aptamer capture probe is a thrombin-binding DNA aptamer;

b) introducing a test sample into the electrophoretic medium;

c) subjecting the electrophoretic medium to an electric field resulting in the electrophoretic migration of the test sample into the electrophoretic medium under conditions suitable for the target molecules to bind to the at least one immobilized aptamer capture probe, wherein the target molecule is human thrombin and is SEQ ID No.1; and d) detecting the presence or absence of target molecule/aptamer capture probe complexes immobilized in the medium, thereby detecting the presence or absence of one or more target molecules in the test sample.

38. The method of claim 37, wherein the concentration of the aptamer capture probe immobilized in the electrophoretic medium is from about 10 to about 100 µM.

39. A method of detecting one or more target molecules in a test sample, comprising the steps of:

a) copolymerizing one or more aptamer capture probes with a material capable of forming a matrix suitable for electrophoresis, wherein said copolymerization forms an electrophoretic medium containing immobilized aptamer capture probes covalently attached to the electrophoretic medium, and wherein said one or more aptamer capture probes are modified with a monomer capable of forming a matrix suitable for electrophoresis;

b) introducing a test sample into the electrophoretic medium;

c) subjecting the electrophoretic medium to an electric field resulting in the electrophoretic migration of the test sample into the electrophoretic medium under conditions suitable for the target molecules to bind to the at least one immobilized aptamer capture probe, wherein the target molecule is selected from the group consisting of: SEQ ID No.2 and SEQ ID No.3; and d) detecting the presence or absence of target molecule/aptamer capture probe complexes immobilized in the medium, thereby detecting the presence or absence of one or more target molecules in the test sample.

40. A method for purifying molecules in a complex test sample comprising target molecules and non-target molecules, comprising:

a) copolymerizing one or more capture probes with a material capable of forming a matrix suitable for electrophoresis, wherein said copolymerization forms an electrophoretic medium containing immobilized capture probes covalently attached to the electrophoretic medium, and wherein said one or more capture probes are modified with a monomer capable of forming a matrix suitable for electrophoresis, and wherein said capture probes are selected from the group consisting of a nucleic acid, modified nucleic acid and a nucleic acid analog, and wherein one or more capture probes are immobilized in a two dimensional array within the electrophoretic medium;

b) introducing a test sample into the electrophoretic medium;

c) subjecting the electrophoretic medium to an electric field resulting in the electrophoretic migration of the test sample through the medium, under conditions and time sufficient for the target molecules to specifically bind to the capture probes, thereby forming target molecule/capture probe complexes, and allowing non-target molecules to migrate through and elute from the medium, wherein only target molecules bind to the capture probes and are immobilized in the medium, thereby subtracting out the target molecule from the sample preparation and purifying molecules in the complex test sample.

41. A method of detecting the presence or absence of one or more target molecules in a test sample, wherein the one or more target molecules has a defined mobility in an appropriate electrophoretic medium when the medium is exposed to an electric field and the target molecule can form binding complexes with capture probes, comprising the steps of:

a) copolymerizing one or more capture probes with a material capable of forming a matrix suitable for electrophoresis to form an electrophoretic medium containing immobilized capture probes covalently attached to the electrophoretic medium, wherein said one or more capture probes are modified with a 5'-acrylamide moiety and are selected from the group consisting of a nucleic acid, modified nucleic acid and a nucleic acid analog, and wherein said one or more capture probes are immobilized in a three dimensional array within the electrophoretic medium;

b) introducing a test sample into the electrophoretic medium;

c) subjecting the electrophoretic medium to an electric field resulting in the electrophoretic migration of the test sample into the region or regions of the electrophoretic medium containing immobilized capture probes, under conditions suitable for the target molecules to bind to the immobilized probes; and d) detecting the presence, or absence of target molecules or target molecule/capture probe complexes immobilized in the medium, thereby detecting the presence or absence of one or more target molecules in the test sample.

42. The method of claim 41, wherein the medium is a gel formed from at least one type of polymer.

43. The method of claim 42, wherein the electrophoretic medium is formed using a polymer of polyacrylamide.

44. The method of claim 41, wherein the capture probes are attached to the acrylamide via a polyethylene glycol spacer group.

45. The method of claim 41, wherein the capture probes are immobilized in a discrete region or regions of the electrophoretic medium.

46. The method of claim 41, wherein the electrophoretic medium contains multiple classes of capture probes, and wherein each class of capture probes is immobilized in a discrete region of the electrophoretic medium.

47. The method of claim 41, wherein the target molecule is selected from the group consisting of: nucleic acids, modified nucleic acids, nucleic acid analogs, proteins, carbohydrates, polysaccharides and small organic molecules.

48. The method of claim 41, wherein the target molecule is either a single-stranded or double-stranded nucleic acid molecule.

49. The method of claim 41, wherein the capture probe is about 5-50 nucleotides in length.

50. A method for purifying or concentrating target molecules from a complex test sample, comprising:

a) copolymerizing one or more capture probes modified with a 5'-acrylamide moiety and selected from the group consisting of a nucleic acid, modified nucleic acid and a nucleic acid analog with a material capable of forming a matrix suitable for electrophoresis to form an electrophoretic medium containing immobilized capture probes covalently attached to the electrophoretic medium, wherein said one or more capture probes are immobilized in a three dimensional array within the electrophoretic medium;

b) introducing a test sample into the electrophoretic medium;

c) subjecting the electrophoretic medium to an electric field resulting in the electrophoretic migration of the test sample through the medium, under conditions and time sufficient for the target molecules in the test sample to specifically bind to the capture probes, thereby forming target molecule/capture probe complexes, and for non-target molecules to migrate through and elute from the medium, wherein only target molecules bind to the capture probes and are immobilized in the medium;

d) treating the electrophoretic medium to release at least one of the following:
    i) the one or more capture probes,
    ii) the target molecules, or
    iii) the target/capture probe binding complexes; and e) eluting the target molecules or target/capture probe complexes from the medium, whereby the released and eluted target molecules are substantially pure.

51. The method of claim 50, wherein the releasing treatment is accomplished by raising the temperature of the medium to a temperature sufficient to denature the target/capture probe complexes.

52. The method of claim 50, wherein the releasing treatment is accomplished by chemical cleavage of the chemical linkage which immobilizes the capture probe within the medium, and the released target molecule/capture probe complex is eluted from the medium.

53. The method of claim 50, wherein the releasing treatment is accomplished by photochemical cleavage of the chemical linkage which immobilizes the capture probe within the medium, and the released target molecule/capture probe complex is eluted from the medium.

54. The method of claim 50, wherein the releasing treatment is accomplished by increasing the electrophoretic field strength.

55. The method of claim 50, wherein the target molecule is selected from the group consisting of: nucleic acids, modified nucleic acids, nucleic acid analogs, proteins, carbohydrates, polysaccharides and small organic molecules.

56. The method of claim 50, wherein the capture probe is about 5-50 nucleotides in length.

57. A method for purifying molecules in a complex test sample comprising target molecules and non-target molecules, comprising:
   a) copolymerizing one or more capture probes modified with a 5'-acrylamide moiety and selected from the group consisting of a nucleic acid, modified nucleic acid and a nucleic acid analog with a material capable of forming a matrix suitable for electrophoresis to form an electrophoretic medium containing immobilized capture probes covalently attached to the electrophoretic medium, wherein said one or more capture probes are immobilized in a three dimensional array within the electrophoretic medium;
   b) introducing a test sample into the electrophoretic medium;
   c) subjecting the electrophoretic medium to an electric field resulting in the electrophoretic migration of the test sample through the medium, under conditions and time sufficient for the target molecules in the test sample to specifically bind to the capture probes, thereby forming target molecule/capture probe complexes and allowing non-target molecules to migrate through and elute from the medium, wherein only target molecules bind to the capture probes and are immobilized in the medium,
   thereby subtracting out the target molecule from the sample preparation and purifying molecules in the complex test sample.

58. A method of detecting the presence or absence of one or more target molecules in a test sample, wherein the one or more target molecules have a defined mobility in an appropriate electrophoretic medium when the medium is exposed to an electric field and the one or more target molecules can form binding complexes with capture probes, comprising the steps of:
   a) copolymerizing one or more capture probes with a material capable of forming a matrix suitable for electrophoresis, wherein said copolymerization forms an electrophoretic medium containing immobilized capture probes covalently attached to the electrophoretic medium, and wherein said one or more capture probes are modified with a monomer capable of forming a matrix suitable for electrophoresis, and wherein said capture probes are selected from the group consisting of a nucleic acid, modified nucleic acid and a nucleic acid analog, and wherein one or more capture probes are immobilized in a three dimensional array within the electrophoretic medium,
   b) introducing a test sample into the electrophoretic medium;
   c) subjecting the electrophoretic medium to an electric field resulting in the electrophoretic migration of the test sample into the region or regions of the electrophoretic medium containing immobilized capture probes, under conditions suitable for the target molecules to bind to the immobilized probes; and
   d) detecting the presence or absence of target molecules or target molecule/capture probe complexes immobilized in the medium,
   thereby detecting the presence or absence of one or more target molecules in the test sample.

59. The method of claim 58, wherein the medium is formed from at least one type of polymer.

60. The method of claim 59, wherein the electrophoretic medium is formed using at least one class of polymers selected from the group consisting of: polyacrylamide, agarose and starch.

61. The method of claim 58, wherein the capture probes are immobilized in a discrete region or regions of the electrophoretic medium.

62. The method of claim 58, wherein the electrophoretic medium contains multiple classes of capture probes, and wherein each class of capture probes is immobilized in a discrete region of the electrophoretic medium.

63. The method of claim 58, wherein the target molecule is selected from the group consisting of: nucleic acids, modified nucleic acids, nucleic acid analogs, proteins, carbohydrates, polysaccharides and small organic molecules.

64. The method of claim 58, wherein the target molecule is either a single-stranded or double-stranded nucleic acid molecule.

65. The method of claim 58, wherein the capture probe is about 5-50 nucleotides in length.

66. A method for purifying or concentrating target molecules from a complex test sample, comprising:
   a) copolymerizing one or more capture probes with a material capable of forming a matrix suitable for electrophoresis, wherein said copolymerization forms an electrophoretic medium containing immobilized capture probes covalently attached to the electrophoretic medium, and wherein said one or more capture probes are modified with a monomer capable of forming a matrix suitable for electrophoresis, and wherein said capture probes are selected from the group consisting of a nucleic acid, modified nucleic acid and a nucleic acid analog, and wherein one or more capture probes are immobilized in a three dimensional array within the electrophoretic medium,
   b) introducing a test sample into the electrophoretic medium;
   c) subjecting the electrophoretic medium to an electric field resulting in the electrophoretic migration of the test sample through the medium, under conditions and time sufficient for the target molecules in the test sample to specifically bind to the capture probes, thereby forming target molecule/capture probe complexes, and for non-target molecules to migrate through and elute from the medium, wherein only target molecules bind to the capture probes and are immobilized in the medium;

d) treating the electrophoretic medium to release at least one of the following:
   i) the one or more capture probe,
   ii) the target molecules, or
   iii) the target/capture probe binding-complexes; and
e) eluting the target molecules or target/capture probe complexes from the medium, whereby the released and eluted target molecules are substantially pure.

67. The method of claim 66, wherein the releasing treatment is accomplished by raising the temperature of the medium to a temperature sufficient to denature the target/capture probe complexes.

68. The method of claim 66, wherein the releasing treatment is accomplished by chemical cleavage of the chemical linkage which immobilizes the capture probe within the medium, and the released target molecule/capture probe complex is eluted from the medium.

69. The method of claim 66, wherein the releasing treatment is accomplished by photochemical cleavage of the chemical linkage which immobilizes the capture probe within the medium, and the released target molecule/capture probe complex is eluted from the medium.

70. The method of claim 66, wherein the releasing treatment is accomplished by increasing the electrophoretic field strength to a level sufficient to disrupt target/capture probe complexes.

71. The method of claim 66, wherein the target molecule is selected from the group consisting of: nucleic acids, modified nucleic acids, nucleic acid analogs, proteins, carbohydrates, polysaccharides and small organic molecules.

72. The method of claim 66, wherein the capture probe is about 5-50 nucleotides in length.

73. A method for purifying molecules in a complex test sample comprising target molecules and non-target molecules, comprising:
   a) copolymerizing one or more capture probes with a material capable of forming a matrix suitable for electrophoresis, wherein said copolymerization forms an electrophoretic medium containing immobilized capture probes covalently attached to the electrophoretic medium, and wherein said one or more capture probes are modified with a monomer capable of forming a matrix suitable for electrophoresis, and wherein said capture probes are selected from the group consisting of a nucleic acid, modified nucleic acid and a nucleic acid analog, and wherein one or more capture probes are immobilized in a three dimensional array within the electrophoretic medium;
   b) introducing a test sample into the electrophoretic medium;
   c) subjecting the electrophoretic medium to an electric field resulting in the electrophoretic migration of the test sample through the medium, under conditions and time sufficient for the target molecules to specifically bind to the capture probes, thereby forming target molecule/capture probe complexes, and allowing non-target molecules to migrate through and elute from the medium, wherein only target molecules bind to the capture probes and are immobilized in the medium,
thereby subtracting out the target molecule from the sample preparation and purifying molecules in the complex test sample.

* * * * *

```
                             SEQUENCE LISTING

<160> NUMBER OF SEQ ID NOS: 7

<210> SEQ ID NO 1
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 1 tttttttta cgcagcgacg agcacgagag                                       30

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: wherein c is modified with fluorescein

<400> SEQUENCE: 2
ctctcgtgct cgtcgctgcg t                                               21

<210> SEQ ID NO 3
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: wherein a is modified with fluorescein

<400> SEQUENCE: 3
attacgttga tattgctgat ta                                              22

<210> SEQ ID NO 4
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: whereiin g is modified with hexylacrylamide-
      (spacer9).sub.6

<400> SEQUENCE: 4
gggttggtgt ggttgg                                                     16

<210> SEQ ID NO 5
<211> LENGTH: 34
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
```

```
<222> LOCATION: (1)..(1)
<223> OTHER INFORMATION: wherein g is modified with hexylacrylamide-
      (Spacer9).sub.6

<400> SEQUENCE: 5
gaattcaaat tgtgagcgga taacaatttg aatt                              34

<210> SEQ ID NO 6
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 6
gaattcaaat tgttatccgc tcacaatttg aattc                             35

<210> SEQ ID NO 7
<211> LENGTH: 30
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: wherein t is modified with hexacrylamide

<400> SEQUENCE: 7 tttttttta cgcagcgacg agcacgagag                                    30
```